US007985742B2

(12) United States Patent  (10) Patent No.: US 7,985,742 B2
Bergeron  (45) Date of Patent: Jul. 26, 2011

(54) SYNERGISTIC COMPOSITIONS OF POLYSACCHARIDES AS NATURAL AND BIODEGRADABLE ABSORBENT MATERIALS OR SUPER ABSORBENTS

(75) Inventor: David Bergeron, La Prairie (CA)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 10/422,881

(22) Filed: Apr. 24, 2003

(65) Prior Publication Data
US 2003/0232965 A1 Dec. 18, 2003

(30) Foreign Application Priority Data
Apr. 24, 2002 (CA) ..................... 2382419

(51) Int. Cl.
A61K 31/715 (2006.01)
A01N 43/04 (2006.01)
C08B 37/00 (2006.01)

(52) U.S. Cl. ............... 514/60; 514/54; 514/55; 514/57; 536/114

(58) Field of Classification Search ............ 514/54, 514/55, 57, 60; 536/114
See application file for complete search history.

(56) References Cited

U.S. PATENT DOCUMENTS

| 2,899,362 | A |   | 8/1959 | Sieger, Jr. et al. ............ 604/368 |
| 3,670,731 | A |   | 6/1972 | Harmon |
| 3,997,484 | A | * | 12/1976 | Weaver et al. ............ 525/54.32 |
| 4,090,013 | A |   | 5/1978 | Ganslaw et al. |
| 4,200,737 | A |   | 4/1980 | Marder et al. |
| 4,410,571 | A |   | 10/1983 | Korpman |
| 4,454,055 | A | * | 6/1984 | Richman et al. ............ 252/194 |
| 4,460,642 | A | * | 7/1984 | Errede et al. ............ 442/351 |
| 4,587,284 | A |   | 5/1986 | Luissi et al. ............ 524/17 |
| 4,693,713 | A |   | 9/1987 | Chmelir et al. |
| 4,826,880 | A |   | 5/1989 | Lesniak et al. |
| 5,221,733 | A |   | 6/1993 | Koskan et al. |
| 5,264,471 | A |   | 11/1993 | Chmelir et al. |
| 5,340,853 | A |   | 8/1994 | Chmelir et al. |
| 5,470,964 | A |   | 11/1995 | Qin |
| 5,498,705 | A |   | 3/1996 | Oin |
| 5,532,350 | A |   | 7/1996 | Cottrell et al. |
| 5,550,189 | A |   | 8/1996 | Qin et al. |
| 5,564,471 | A |   | 10/1996 | Wilder et al. |
| 5,612,384 | A |   | 3/1997 | Ross et al. |
| 5,718,770 | A |   | 2/1998 | Shah et al. |
| 5,720,822 | A |   | 2/1998 | Jeffcoat et al. |
| 5,721,295 | A |   | 2/1998 | Bruggemann et al. |
| 5,736,595 | A |   | 4/1998 | Gunther et al. |
| 5,789,570 | A |   | 8/1998 | Buchholz et al. |
| 5,801,116 | A | * | 9/1998 | Cottrell et al. ............ 502/404 |
| 5,847,031 | A |   | 12/1998 | Klimmek et al. |
| 5,858,392 | A |   | 1/1999 | Dumitriu et al. ............ 424/443 |
| 5,932,017 | A |   | 8/1999 | Chiu et al. |
| 5,985,432 | A |   | 11/1999 | Wang et al. |
| 6,016,574 | A |   | 1/2000 | Chen |
| 6,033,769 | A |   | 3/2000 | Brueggemann et al. |
| 6,051,317 | A |   | 4/2000 | Brueggemann et al. |
| 6,063,914 | A | * | 5/2000 | Wolf et al. ............ 536/107 |
| 6,107,432 | A | * | 8/2000 | Engelhardt et al. ............ 527/311 |
| 6,121,509 | A |   | 9/2000 | Ashraf et al. |
| 6,231,675 | B1 |   | 5/2001 | Chiu et al. |
| 6,261,376 | B1 |   | 7/2001 | Jeffcoat et al. |
| 6,277,186 | B1 |   | 8/2001 | Shi et al. |
| 6,309,661 | B1 |   | 10/2001 | Haynes et al. ............ 424/426 |
| 6,441,266 | B1 |   | 8/2002 | Dyer et al. |
| 6,444,653 | B1 |   | 9/2002 | Huppe et al. |
| 6,451,121 | B2 |   | 9/2002 | Chiu et al. |
| 2002/0019447 | A1 |   | 2/2002 | Renn et al. |
| 2002/0156048 | A1 |   | 10/2002 | Huppe et al. |
| 2002/0193516 | A1 |   | 12/2002 | Bucevschi et al. |

FOREIGN PATENT DOCUMENTS

| CA | 2308537 | 11/2000 |
| CA | 2362006 | 5/2002 |
| EP | 0393825 | 10/1990 |
| EP | 0 691 133 A1 | 1/1996 |
| GB | 1207352 | 9/1970 |
| WO | WO 94/17137 A1 | 8/1994 |
| WO | WO 95/11925 A1 | 5/1995 |
| WO | WO 97/25463 A1 | 7/1997 |
| WO | WO 99/29352 A1 | 6/1999 |
| WO | WO 00/35504 A1 | 6/2000 |
| WO | WO 00/67809 | 11/2000 |
| WO | WO 0067809 A1 * | 11/2000 |
| WO | WO 01/34656 A1 | 5/2001 |
| WO | WO 01/87365 A2 | 11/2001 |
| WO | WO 02/09653 | 2/2002 |
| WO | WO 02/15687 A2 | 2/2002 |
| WO | WO 02/096953 | 12/2002 |

OTHER PUBLICATIONS

European Search Report, issued in European Patent Application No. 03717079, dated Jun. 12, 2007.
Edana, Centrifuge Retention Capacity No. 440.1-99, Recommended Test Method: Superabsorbent materials—Polyacrylate superabsorbent powders—Free Swell Capacity in saline by gravimetric determination, Feb. 1999.
Eidam D.(A); Kulicke W.-M. (A); Kuhn K.; "Formation of maize starch gels selectively regulated by the addition of hydrocolloids", Starch, 47 (10), 1995, pp. 378-384.
Garcia R.B.; Andrade C.T. "Evidence of interaction between agarose and guar gum from changes in network response to solvent perturbation" Carbohydrate Polymers, 34 (3), 1997, pp. 157-163.

(Continued)

Primary Examiner — Shaojia Anna Jiang
Assistant Examiner — Everett White

(57) ABSTRACT

A multi-component synergistic absorbent composition includes at least one polysaccharide and at least one or more polysaccharide-based components or gelling proteins. This composition possesses synergistic effects in its capacity to absorb water, saline solutions and biological fluids, at normal pressure or under load, or to retain these fluids, or a combination of these properties.

7 Claims, 10 Drawing Sheets

OTHER PUBLICATIONS

Goycoolea F.M.; Foster T.J.; Richardson R.K.; Morris E.R.; Gidley M.J. "Synergistic gelation of galactomannans or Koniac glucomannan: binding or exclusion" Gums and stabiliziers for the food industry 7: Proceedings of the 7th international conference, Wrexham, 1993, pp. 333-344.

Kaletung-Gencer G.; Peleg M. "Rheological characteristics of selected food gum mixtures in solution" Journal of Texture Studies, 17 (1), 1986, pp. 61-70.

Kovacs P. "Useful incompatibility of xanthan gum with galactomannans" Food Technology, 27 (3), 1973, pp. 26-30.

Murayama A.; Ichikawa Y., Kwabata A. "Rheological properties of mixed gels of kappa-carrageenan with galactomannan", Bioscience Biotechnology and Biochemistry, 59 (1), 1995, pp. 5-10.

Pellicer J.; Delegido J.; Dolz J.; Dolz M; Hernandez M.J.; Herraez M. "Influence of shear rate and concentration ratio on viscous synergism. Application to xanthan-locust bean gum—NaCMC mixtures" Food Science and technology international, 6 (5), 2000, pp. 415-423.

Perry, J.H.; Perry R.: Chilton C.; Kirkpatrick S.; "Chemical Engineers' Handbook" Fourth Edition, McGraw Hill, 1963.

Prabhanjan H.; Ali S.Z. "Studies on Rheological properties of tamarind kernel powder, its derivatives and their blends with maize starch" Carbohydrate Polymers, 28 (3), 1995, pp. 245-253.

"Modern Superabsorbent Polymer Technology" (Buchholz F.L., Graham A.T., Eds Wiley-VCH, New-York, 1998, ISBN 0-471-19411-5.

Alloncle M.; Doublier J.-L. "Viscoelastic properties of maize stach/hydrocolloid pastes and gels" Food Hydrocolloids, 5 (5), 1991, pp. 455-467.

Alloncle M.; Lefebvre J.; Llamas G.; Doublier J.L. "A Rheological characterization of cereal starch-galactomannan mixtures". Cereal Chemistry, 66 (2), 1989, pp. 90-93.

ASTM D 6355-98 (Reapproved 2003), Standard Test Method for Human Repeat Insult Patch Testing of Medical Gloves.

Beenackers A.A.C.M. et al. Carbohydrate Polymers, 45, 2001, pp. 219-226.

Christianson D.D. "Hydrocolloid interactions with starches" Food Carbohydrates: A symposium, 1982, pp. 399-419.

Christianson D.D.; Hodge J.E.; Osborne D.: Detroy R.W. "Gelatinization of wheat starch as modified by xanthan gum, guar guam and cellulose gum", Cereal Chemistry, 58 (6), 1981, pp. 513-517.

Doublier J.-L.; Castelain C.; Lefebvre J. "Viscoelastic properties of mixed polysaccharides systems" Plant polymeric carbohydrates : Proceedings of a symposium, Berlin, Jul. 1992, pp. 76-85.

Edana, Absorbency Against Pressure No. 442.1-99, Recommended Test Method: Superabsorbent materials—Polyacrylate superabsorbent powders—Absorbency Against Pressure by Gravimetric determination, Feb. 1999.

Edana, Centrifuge Retention Capacity No. 441.1-99, Recommended Test Method: Superabsorbent materials—Polyacrylate superabsorbent powders—Centrifuge Retention Capacity in Saline by Gravimetric Determination, Feb. 1999.

Rayment R.; Rossmurphy SB.; Ellis PR. "Rheological properties of guar galactomannan and starch mistures 1. Steady shear measurements" Carbohydrate polymers, 28 (2), 1995, pp. 121-130.

Riccardo, PO, "Water-absorbent polymers: A patent survey", J.Macromol.Sci., Rev.Macromol.Chem.Phys., C34 (04), 1994, pp. 607-662, ISSN 0736-6574.

Schorsch C.; Garnier C.; Doublier J.-L. "Viscoelastic properties of xanthan/galactomannan mixtures: Comparison of guar with locust bean gum" Carbohydrate Polymers, 34 (3), 1997, pp. 165-175.

Sudhakar V(A); Singhal RS; Kulkarni P.R. "Starch-galactomannan interations: functionality and rheological aspects.", Food Chemistry, 55 (3), 1996, pp. 259-264.

Sudhakar, V.; Singhal, R.S.; Kulkarni P.R., "Effect of salts on interactions of starch with guar gum" Food Hydrocolloids, 10 (3), 1996, pp. 329-334.

Tako M. "Synergistic interaction between xanthan and Konjac glucomannan in aqueous media" Bioscience, Biotechnology, and biochemistry, 56 (8), 1992, pp. 1188-1192.

Tako M.; Nakamura S. "Synergistic interaction between agarose and D-galacto-D-mannan in aqueous media" Agricultural and biological chemistry, 52 (4), 1988, pp. 1071-1072.

United-States Environmental Protection Agency (EPA), Fate, Transport and Transformation Test Guidelines, OPPTS 835.3200 Zahn-Wellens/EMPA Test, Public Draft, EPA 712-C-96-084, Apr. 1996.

* cited by examiner

SYNERGISTIC COMPOSITIONS OF POLYSACCHARIDES AS NATURAL AND BIODEGRADABLE ABSORBENT MATERIALS OR SUPER ABSORBENTS

FIELD OF THE INVENTION

The present invention relates to synergistic compositions of polysaccharides as natural and biodegradable absorbent materials or superabsorbents. The compositions of the present invention show synergistic effects in their capacity to absorb water, saline solutions, biological fluids, and the like, at normal pressure or under load, and to retain these fluids.

BACKGROUND

Superabsorbent polymers are mainly used as absorbents for biological fluids, water, aqueous solutions and the like. These absorbents are primarily used in diapers, adult incontinence products as well as in feminine hygiene applications. Polyacrylates and polyacrylamides, as well as their copolymers, are among the best known superabsorbents. Alternative acrylic superabsorbent polymer forms, including partially biodegradable materials, are described in "*Modern Superabsorbent Polymer Technology*" (Buchholz F. L. and Graham A. T. Eds., Wiley-VCH, New York, 1998).

Commercial superabsorbents are mainly polyacrylate-based polymers. However, their biodegradability is questionable, especially for high molecular weight polymers. These polymers are synthesized from monomers such as acrylic acids and acrylamides. Following the polymerization process, there are still residual monomers or oligomers showing toxicity and allergenic potential.

These synthetic polymers have also been grafted onto polysaccharides. Superabsorbent polysaccharide-based grafted-polymers are obtained through the grafting of an unsaturated monomer (acrylonitrile, acrylic acid, acrylamide) onto starch or, less frequently, cellulose. The so-obtained polymers, also called "Super Slurper", illustrate a water absorption capacity ranging from 700 to 5300 g/g for deionised water, and up to 140 g/g in a 0.9% saline solution (weight by volume of NaCl, referred hereinafter as saline solution) (Riccardo P. O., Water-Absorbent Polymers: A Patent Survey. J. Macromol. Sci., Rev. Macromol. Chem. Phys., 1994, 607-662 (p.634) and cited references). Despite their high water absorption capacity, these grafted polysaccharides, prepared by radical polymerization, are hypoallergenic and are not known to be biodegradable.

Among other polymers, polyaspartates have been recognized as offering good absorbent properties and as being biodegradable (Ross et al., U.S. Pat. No. 5,612,384). However, polyaspartates appear to have several drawbacks regarding their low molecular weight. Furthermore, polyaspartates are produced synthetically (Koskan et al., U.S. Pat. No. 5,221,733) from non-renewable sources such as for example maleic anhydride (obtained from butane). Finally, these polymers are strongly ionic and subject to performance fluctuations in saline solutions.

Polymeric blends and mixtures, used as absorbents or superabsorbents, are known. More specifically, the synergistic effect on the absorption against pressure of two synthetics polyacrylate-based hydrogel-forming particles has been reported (Schmid et al., EP 0 691 133 A1). Since these formulations comprise synthetic polymers, they are unsuitable in light of allergenic, abrasive, ecological or toxicological concerns.

Chmelir and Klimmek (U.S. Pat. No. 5,340,853), teach a synergistic absorbing and swelling agent consisting of at least two components. The agent is made from a water-swellable synthetic polymer or copolymer, crosslinked with a multifunctional compound, and a second component. The second component is a polysaccharide such as galactomannans or polygalactomannans. Alternatively, it could comprise admixtures of a galactomannan or polygalactomannans with other natural or synthetic polymers such as starch and modified starch. Even though the inventors refer to a synergistic effect when mixing the two components, no clear evidence for the synergy has been demonstrated when only polysaccharide components are used. Furthermore, since these formulations require synthetic polymers, such as polyacrylates, they are unsuitable for many uses in light of allergenic, abrasive, ecological or toxicological concerns.

Many other polyacrylate-polysaccharide based synergistic compositions have been disclosed such as those taught by Gunther, Klimmek, Brüggeman and Chmelir (U.S. Pat. Nos. 5,721,295; 5,847,031; 5,736,595; 5,264,471; and 4,693,713 Reissue 33,839). However, since these formulations again require synthetic polymers, such as polyacrylates, they are unsuitable in light of allergenic, abrasive, ecological or toxicological concerns.

Renewable resources such as mixtures of polysaccharides have also been considered as absorbent materials. U.S. Pat. No. 5,801,116, granted to Rhodia Inc. (Cottrell et al.) discloses one or more polysaccharides having a particle size of greater than 200 mesh (74 microns), preferably modified guar gum. This modified guar gum may be used alone as an absorbent material or in combination with other known materials, such as natural or synthetic hydrophilic polymers. The inventors describe a potential synergistic absorbency when the compositions are combined with one or more of several classes of chemicals including simple carbohydrates (glucose, fructose, sorbitol, and the like) and synthetic hydrophilic polymers. However, no specific composition is exemplified to prove the synergistic hypothesis. Furthermore, these guar absorbents have an undesirable tendency to give an syneresis effect (referred as slimy effect) to the wearer.

U.S. Pat. No. 4,454,055 (Richman et al.), issued to National Starch, teach synergistic interactions between ionically crosslinked polyelectrolytes (polyacrylates-starches), and modified starches or other extenders. Because these ionically crosslinked polyelectrolytes are made mainly from synthetic SAPs (Super Absorbent Polymers), they are again unsuitable for many uses in light of allergenic, abrasive, ecological or toxicological concerns.

Polysaccharide-protein synergies have also been reported in the food industry. The synergistic compositions relate to the viscosity or texture enhancement of food gels (Alloncle M et al., Cereal Chemistry, 66 (2), 1989, pp. 90-93; Kaletung-Gencer G et al., Journal of Texture Studies, 17 (1), 1986, pp. 61-70; Alloncle M et al., Food Hydrocolloids, 5 (5), 1991, pp.455-467; Sudhakar V et al., Food Chemistry, 55 (3), 1996, pp. 259-264; Rayment P et al., Carbohydrate polymers, 28 (2), 1995, pp. 121-130; Pellicer J et al., Food Science and Technology International, 6 (5), 2000, pp. 415-423; Tako M, Bioscience Biotechnology and Biochemistry, 56 (8), 1992, pp. 1188-1192; Tako M et al., Agricultural and Biological Chemistry, 52 (4), 1988, pp.1071-1072; Murayama A et al., Bioscience, Biotechnology and Biochemistry, 59 (1), 1995, pp. 5-10; Goycoolea F. M et al., Gums and stabilizers for the food industry 7: proceedings of the 7th international conference in Wrexham, July, 1993, pp. 333-344). The reasons for being of these food gels is different when compared to those used in hygiene applications. Food gels aren't designed to absorb or retain large amounts of saline or physiological fluids under pressure. Indeed, no synergistic effects have been reported in these publications concerning absorbent or superabsorbent technologies.

Glass-like, pregelatanized starches, have been disclosed by Groupe Lysac (Huppé et al. C A U.S. Pat. No. 2,308,537) as being a useful absorbent for liquids. However, these pregelatinized starches only absorb 8 g/g, which is too low to be useful in the hygiene industry. In order to improve the absorption capacity of these modified starches, they were mixed with xanthan and guar gums. The modified starches have also been blended in mixtures with sodium carboxymethyl cellulose (CMC). Some synergistic effects were observed but only in those cases where starches were admixed with specific concentrations of guar and xanthan gums. Moreover, the disclosed absorption capacities remained too low to be useful in the hygiene industry.

There thus remains a need for novel synergistic compositions of polysaccharides with improved performance as natural and biodegradable absorbent materials or superabsorbents.

The present invention seeks to meet these and other needs.

The present invention refers to a number of documents, the content of which is herein incorporated by reference in their entirety.

SUMMARY

The present invention relates to synergistic compositions of polysaccharides as natural and biodegradable absorbent materials or superabsorbents. These synergistic compositions show an increased capacity to absorb liquids such as water, saline solutions and biological fluids, at normal pressure or under load, and to retain these fluids. Furthermore these synergistic compositions are based on natural sources, are biodegradable and non-toxic. More specifically, the present invention relates to synergistic absorbent or superabsorbent compositions comprising at least one polysaccharide and at least one polysaccharide-based component or gelling protein.

The present invention relates to synergistic compositions of polysaccharides to be used as natural, renewable and biodegradable absorbents or superabsorbents for personal hygiene products such as baby diapers, incontinence products and sanitary napkins. The compositions can also be used in several other applications such as in food packaging absorbent pads; in agricultural and forestry applications to retain water in the soil and to release water to the roots of plants; in fire-fighting techniques; as bandages and surgical pads; for cleaning-up acidic or basic aqueous solution spills, including water soluble chemical spills; as polymeric gels for cosmetics and pharmaceuticals also known as drug delivery systems for the controlled release of active substances and; and finally for manufacturing artificial snow.

The present invention also relates to a multi-component synergistic absorbent composition comprising one or more modified starches and at least one or more components selected from a first component class selected from mannose containing polysaccharides, a second component class selected from ionic polysaccharides, and a third component class selected from gelling proteins or polypeptides.

The present invention further relates to a multi-component synergistic absorbent composition comprising one or more ionic polysaccharides and at least one or more components selected from a first component class selected from mannose containing polysaccharides and a second component class selected from gelling proteins or polypeptides.

Further scope and applicability will become apparent from the detailed description given hereinafter. It should be understood, however, that this detailed description, while indicating preferred embodiments of the invention, is given by way of example only, since various changes and modifications will become apparent to those skilled in the art.

DETAILED DESCRIPTION

Figure 1:
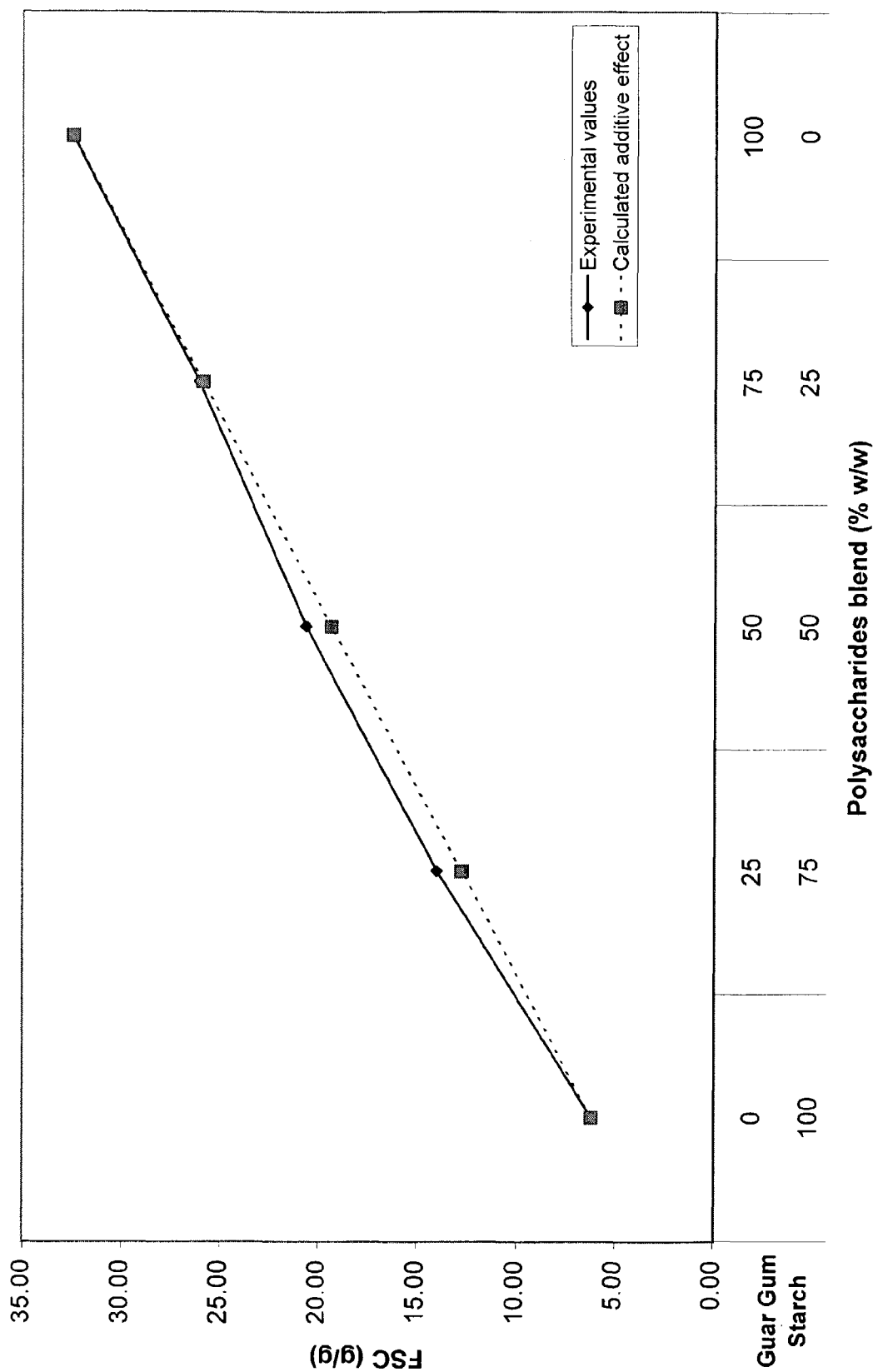
FIG. 1 shows a comparison between measured FSC values and calculated additive values in 0.9% NaCl solution for different ratios of guar gum and starch. A weak synergistic effect is observed when higher values are obtained as compared to the corresponding calculated additive values.

The present description refers to a number of routinely used chemical terms. Nevertheless, definitions of selected terms are provided for clarity and consistency.

As used herein the term polysaccharide refers to a combination of nine or more monosaccharides, linked together by glycosidic bonds, and include starch, modified starch, cellulose, etc.

As used herein, the term "modified" starch means a starch that is pregelatinized, thermally inhibited [Jeffcoat et al. (U.S. Pat. Nos. 5,720,822; 6,261,376; 6,016,574), Chung-Wai et al. (U.S. Pat. Nos. 5,932,017; 6,231,675; 6,451,121), Shah et al. (U.S. Pat. No. 5,718,770), Shi et al. (U.S. Pat. No. 6,277,186)], extruded, jet-cooked, dextrinated, hydrolyzed, oxidized, covalently cross-linked, alkylated, hydroxyalkylated, carboxyalkylated, esterified, fractionated in its amylose or amylopectin constituents.

As used herein, the term "Free Swell Capacity" (FSC), also called Absorption, refers to the amount (g) of fluid absorbed (0.9% Weight/volume NaCl solution, thereafter called 0, 9% NaCl solution) per gram of the composition.

As used herein, the term "Centrifuge Retention Capacity" (CRC) also called Retention, refers to the amount (g) of fluid absorbed (0.9% NaCl solution) per gram of the composition.

As used herein, the term "Absorption Under Load" (AUL) at 0.3 PSI (2.06 KPa), also called Absorption Against Pressure, refers to the amount (g) of substance absorbed (0.9% NaCl solution) per gram of the composition, using 0.1 g of absorbent in the apparatus.

As used herein, the term "ionic polysaccharides" refers to both anionic or cationic polysaccharides.

In a broad sense, the present invention relates to synergistic compositions of polysaccharides as natural and biodegradable absorbent materials or superabsorbents. It was discovered that the absorbing characteristics of modified starches can be synergistically improved by the addition of a polysaccharide composed of mannose, an ionic polysaccharide, gelling proteins or a combination thereof. Furthermore, it was discovered that the performances of ionic polysaccharides can be improved by the addition of mannose containing polysaccharides, gelling proteins or a combination thereof.

Examples of anionic polysaccharides are selected from the group consisting of sodium, lithium, potassium, and ammonium salts of carboxyalkylated cellulose (like carboxymethyl cellulose), as well as oxidized cellulose, pectin, arabic gum, kappa, iota or lambda carrageenans, agar-agar or alginates. Examples of cationic polysaccharides are selected from the group consisting of chloride, bromide, iodide, nitrate, phosphates, sulfates and organic salts of chitosan, as well as cationic cellulose.

These polysaccharide compositions, in order to be suitable for absorption purposes, should have a mean particles size ranging from about 80 µm to about 800 µm and more preferably from about 150 µm to about 600 µm. In order to avoid particle migration, the particles should be homogeneously blended. In order to achieve a homogeneous blending, the size of the particles should not vary by more than about 200 µm. A process for producing the compositions is provided.

The absorbent or superabsorbent synergistic polysaccharides compositions, in accordance with the present invention, are prepared with different ratios of individual components, as illustrated in Examples 1 to 57. These compositions are then characterized by their Free Swell Capacity (FSC), their Centrifuge Retention Capacity (CRC) as well as their Absorption Under Load (AUL) capacity at 0.3 PSI (2.06 KPa). The FSC and CRC are standard methods in the field of superabsorbents, used for all applications in personal hygiene. AUL is a standard test for baby diapers.

A synergistic effect for a multi-component system is observed when the measured value of the AUL, FSC and CRC is higher than the calculated additive value.

Typical compositions of polysaccharides, as disclosed in the present invention, are represented by the following equation:

$$A_a + B_b + N_n = 1$$

wherein, A is the composition fraction (weight by weight or referred to hereinafter as W/W) of modified starch or ionic polysaccharides, when these polysaccharides are used as the primary constituent; B represents the composition fraction (W/W) of a mannose containing polysaccharide, a gelling protein or an ionic polysaccharide (when starch is the primary constituent of the composition); N represents the composition fraction (W/W) of supplemental constituents, these constituents being composed of one or more polysaccharides or proteins, selected from mannose containing polysaccharides, gelling proteins, ionic polysaccharides or modified starches (when applicable). It is important to note that N is a optional number and it is contemplated that as many Ns as required can be used in order to improve the synergistic effects.

A specific CRC, AUL and FSC can be attributed to each component. In other words, the first component of the synergistic blend has an AUL, FSC, and CRC value corresponding to $AUL_a$, $FSC_a$ and $CRC_a$, and has a composition fraction (W/W) A. The second component has a composition fraction (W/W) B, and has $AUL_b$, $FSC_b$ and $CRC_b$ values. Other optional components have a composition fraction (W/W) N, and $AUL_n$, $FSC_n$, and $CRC_n$ values.

The Absorption Under Load (AUL), the Free Swell Capacity (FSC), and the Centrifuge Retention Capacity (CRC) of the blends, [$AUL_{a+b+n}$, $FSC_{a+b+n}$ and $CRC_{a+b+n}$] can be calculated and expressed as follows:

$$AUL_{a+b+n} = A \cdot AUL_a + B \cdot AUL_b + N \cdot AUL_n$$

$$FSC_{a+b+n} = A \cdot FSC_n + B \cdot FSC_b + N \cdot FSC_n$$

$$CRC_{a+b+n} = A \cdot CRC_n + B \cdot CRC_b + N \cdot CRC_n$$

A synergistic effect is observed when the measured AUL, FSC and CRC results of the composition are higher that the calculated additive ones, [$AUL_{a+b+n}$, $FSC_{a+b+n}$ and $CRC_{a+b+n}$].

Synergistic effects were observed in many complex polysaccharide compositions comprising at least one polysaccharide and at least one or more polysaccharide-based components or gelling proteins. These synergistic effects occur more often, and are more important, when three or more compounds selected from these classes are present in the composition. These synergistic effects are also more important when the primary constituent of the composition is selected from the class of modified starches or ionic polymers. Significant synergistic effects are also observed when more then one product of a same class is used.

The first component class of the compositions of the present invention can be selected from the modified starches. These modified starches can be obtained from diversified sources, such as corn, waxy corn, wheat, waxy wheat, rice, waxy rice, potato, tapioca, waxy maize, sorghum, waxy sorghum, sago, barley, and amaranth. In order to be useful for the applications as contemplated by the present invention, these modified starches can be dextrinated, hydrolyzed, oxidized, covalently crosslinked, alkylated, hydroxyalkylated, carboxyalkylated, carboxymethylated, acetylated or esterified, fractionated (e.g. amylose and amylopectin), and physically modified by thermal inhibition, jet-cooking or extrusion.

Oligomeric polyethylene glycol crosslinked polysaccharides have been previously described by Groupe Lysac (Couture et al., C A U.S. Pat. No. 2,362,006) as being particularly useful as modified starches. Other examples of physically modified starches have been described by Groupe Lysac (Huppé et al., CA U.S. Pat. No. 2,308,537). In the latter, a pregelatinized, glass-like starch was disclosed, which was subsequently found to be useful as a modified starch for the compositions of the present invention.

Other modified starches, such as those disclosed by Kimberly-Clark (Qin et al., U.S. Pat. Nos. 5,550,189; 5,498,705, and 5,470,964), SCA (Besemer et al., WO 00/35504A1, WO 01/34656A1 and WO 99/29352A1), Beenackers A. A. C. M. et al. (Carbohydr. Polym., 2001, 45, 219-226) and National Starch (Jeffcoat et al. U.S. Pat. Nos. 5,720,822; 6,261,376; 6,016,574; Chung-Wai et al. U.S. Pat. Nos. 5,932,017; 6,231, 675; U.S. Pat. No. 6,451,121; Shah et al. U.S. Pat. No. 5,718, 770; Shi et al. U.S. Pat. No. 6,277,186), could also be used in the compositions of the present invention. These modified starches constitute only a few examples of modified starches useful for the absorbent compositions of the present invention. Because these modified starches already have some absorbent properties, and exhibit less syneresis (slimy effect) than other polysaccharides, they are preferred as the primary constituent of the compositions of the present invention.

The second component class of the compositions of the present invention can be selected from the mannose containing polysaccharides. These polysaccharides comprise glucomannans or polyglucomannans such as konjac gum, or konjac flour. This class also comprises galactomannans or polygalactomannans, such as Guar gum, Locust bean gum, Mesquite gum, Tara gum, Phylium extracts and Fenugreek extracts, in addition to comprising Aloe mannans.

The mannose containing polysaccharides can be used in their natural, unmodified form as well as in a physically or chemically modified form. The mannose containing polysaccharides can be hydrolyzed, oxidized, covalently crosslinked, alkylated, hydroxyalkylated, carboxyalkylated, carboxymethylated, acetylated or esterified, and physically modified by extrusion, jet-cooking or other processes.

The third component class of the compositions of the present invention is an ionic polysaccharide-based compound. Ionic polysaccharides can be both anionic and cationic. Examples of suitable cationic polysaccharides are selected from the group consisting of chlorides, bromides, iodides, nitrates, sulfates, phosphates and organic salts of cationic polysaccharides, as well as cationic cellulose or chitosan salts.

Anionic polysaccharides are the preferred third component class for the compositions of the present invention. They can be in their sodium, lithium, potassium or ammonium salt forms. Sodium carboxymethyl cellulose (CMC) is the preferred ionic component. Other useful ionic polysaccharides are sodium alginate and alginate compositions, xanthan gum, kappa, iota and lambda carageenan gums, karaya gum, arabic gum, pectin, agar-agar, oxidized cellulose and sulfated cellulose.

The ionic polysaccharides can be used in their natural, unmodified form, as well as in a physically or chemically modified form. The ionic polysaccharides can be hydrolyzed, oxidized, covalently crosslinked, alkylated, hydroxyalkylated, carboxyalkylated, carboxymethylated, acetylated or esterified, and physically modified by extrusion, jet-cooking or other processes.

Since the ionic polysaccharides exhibit high absorption properties, they are also the preferred primary constituent for the compositions of the present invention.

The fourth component class of the compositions of the present invention are gelling proteins or polypeptides. Because these compounds are biodegradable and based on renewable sources, they provide a wide array of synergistic effects suitable to the compositions of the present invention. Examples of suitable gelling proteins or polypeptides are gelatin, collagen, albumin, ovalbumin, bovine albumin, casein, keratin, keratose, Whey proteins, Whey proteins isolates, soybean proteins, soy proteins, soy proteins isolate, polyaspartic acid or its salts, zein and gluten. Preferred gelling proteins are gelatin, as well as casein and its salts.

The gelling proteins can be used in their natural, unmodified form, as well as in a physically or chemically modified form. The gelling proteins can be hydrolyzed, oxidized, covalently crosslinked, alkylated, hydroxyalkylated, carboxyalkylated, carboxymethylated, acetylated or esterified, and physically modified by extrusion, jet-cooking or other processes.

In order to provide the desired synergistic effects, the selected compounds must be homogeneously mixed. Mixing techniques are widely known in the art and are described in Perry's Chemical Engineers' Handbook ($7^{th}$ edition, McGraw-Hill, 1997, ISBN: 0070498415).

Typical compositions can be mixed using double cone mixers, twin shell mixers, horizontal drum (with or without baffles), double cone revolving around long axis (with or without baffles), ribbon mixers, vertical screw mixers, batch Muller mixers, continuous Muller mixers, twin rotor mixers, single rotor or turbine mixers. Other mixing techniques applicable to the compositions of the present invention will become apparent to a skilled technician in the art, and are contemplated as being within the scope of the present invention.

The polysaccharides and gelling proteins should have a specific particle size in order for the compositions to be suitable for absorption purposes. The mean particulate size of these components should not be below 80 μm, in order to avoid fine particulate problems (Occupational Safety and Health problems). In order to facilitate water, saline or physiological fluid penetration inside the particulates (to avoid a phenomenon called gel blocking), the particulates should not have a mean particulate size greater than 800 μm. Particularly efficient synergistic compositions were obtained with mean particulate sizes ranging from about 150 μm to about 600 μm.

In order to obtain homogenous compositions the additional components (like B or N components) should have a similar mean particulate size. Particulate migration can be avoided if the size of the additional components of the compositions does not vary by more than 200 μm from the primary component (modified starches or, when no modified starches are used, ionic polysaccharides).

The absorbent materials or superabsorbents described in the present invention, may be incorporated into absorbent personal hygiene products such as, for example, baby diapers, incontinence products, sanitary napkins and the like. They could be also used in absorbent members, like absorbent cores, airlaids or foamed structures. These absorbent members are mainly made from superabsorbents, cellulosic fibers or man-made fibers and bi-component thermoplastic fibers (known also as BICO).

Furthermore, the absorbent compositions could also be used in several other applications, such as in food pads; in agricultural and forestry applications to retain water in the soil and to release water to the roots of plants; in fire-fighting techniques; as bandages and surgical pads; for cleanup of acidic or basic aqueous spills, including water soluble chemical spills; as polymeric gels for cosmetics and pharmaceuticals (also known as drug delivery systems) for the controlled release of active substances; and for artificial snow.

As was previously mentioned, a synergistic effect for a multi-component polysaccharide system is observed when the measured value of the AUL, FSC and CRC is higher than the calculated additive value. This can be observed when at least two or more compound classes are used together. More specifically, synergistic effects were observed in many complex polysaccharide compositions comprising at least one polysaccharide and at least one or more polysaccharide-based components or gelling proteins.

Figure 2:
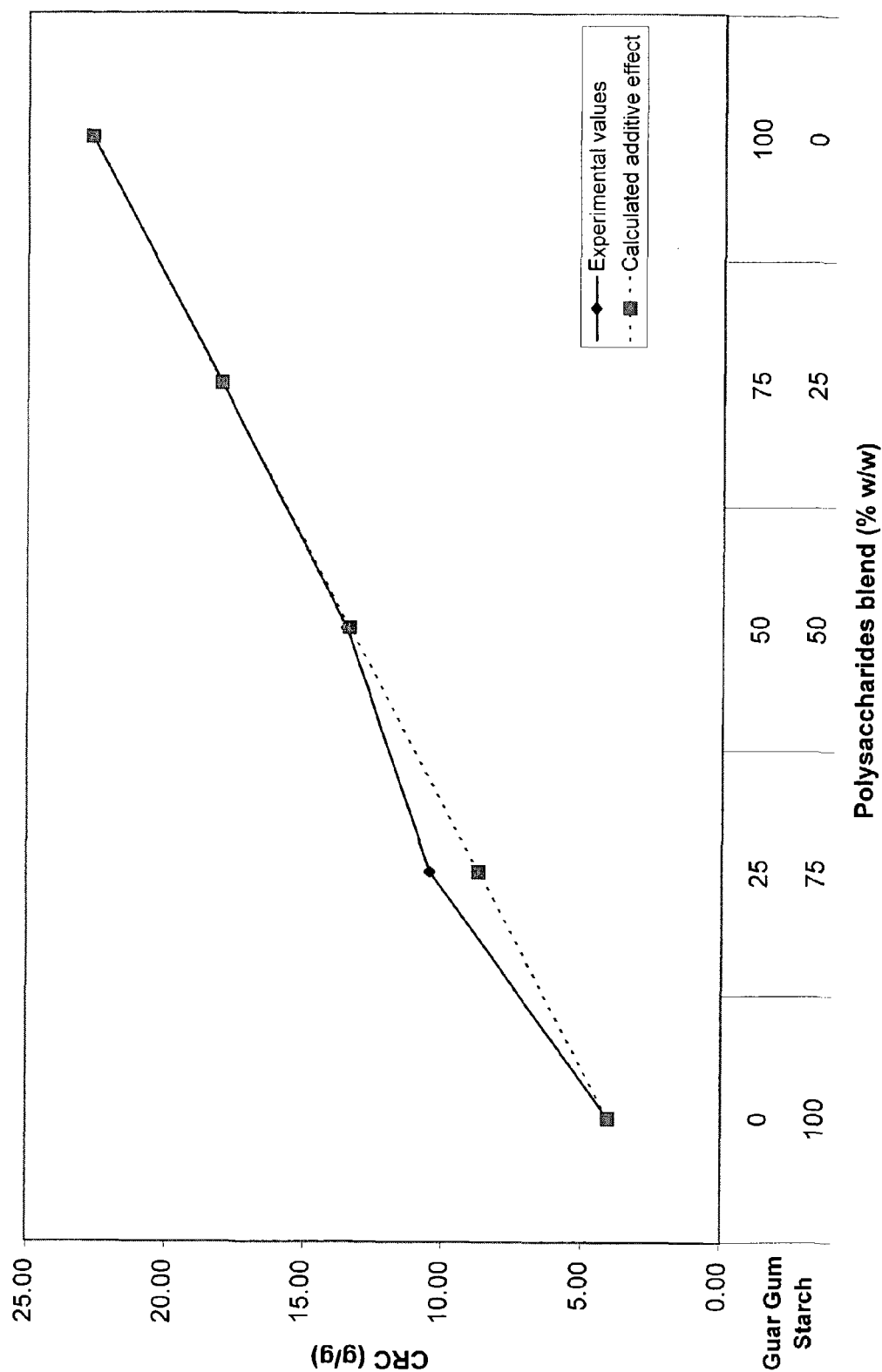
FIG. 2 shows a comparison between measured CRC values and calculated additive values in 0.9% NaCl solution for different ratios of guar gum and starch. A weak synergistic effect is observed when higher values are obtained as compared to the corresponding calculated additive values.
Figure 3:
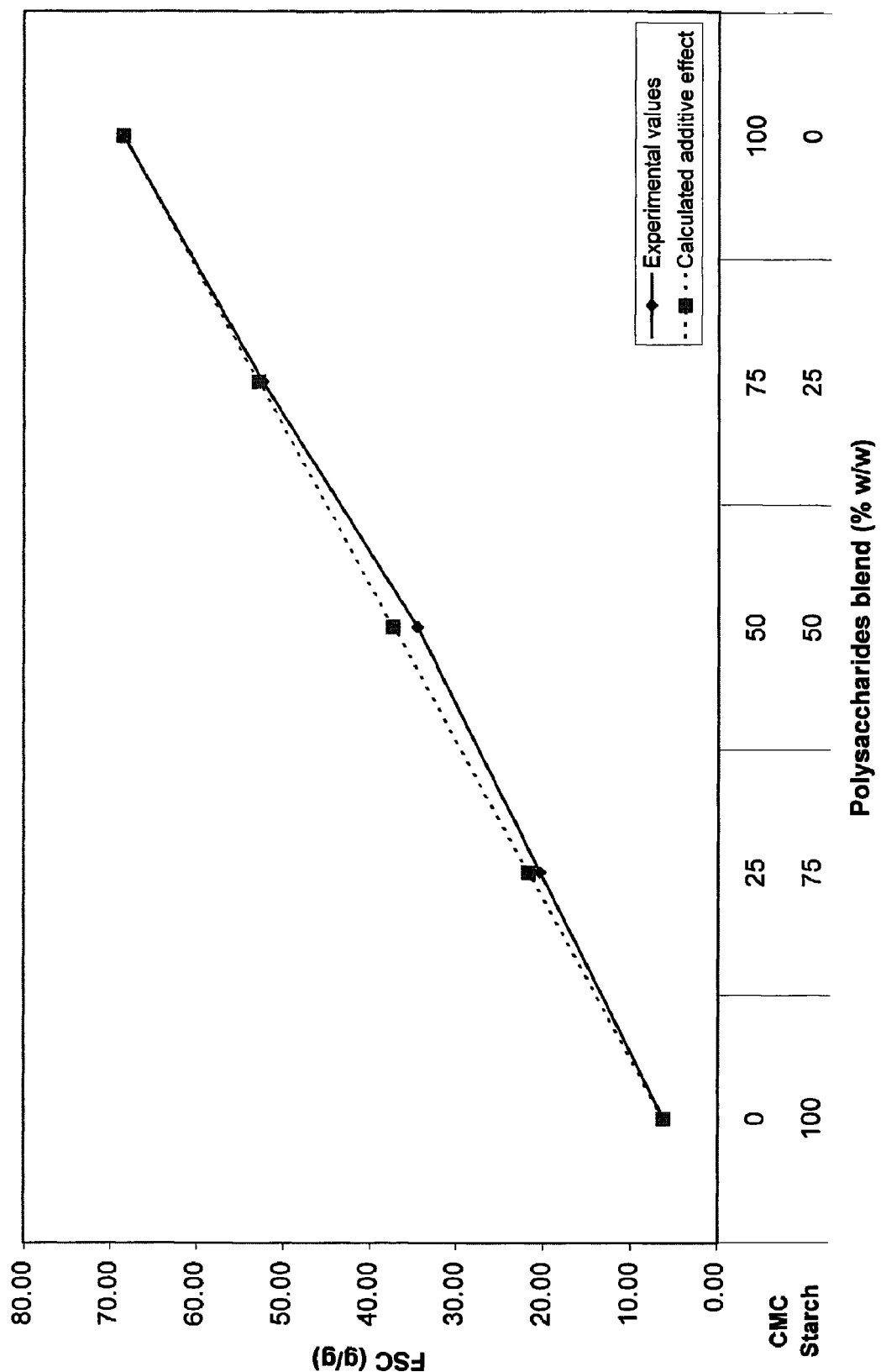
FIG. 3 shows a comparison between measured FSC values and calculated additive values in 0.9% NaCl solution for different ratios of CMC and starch. No synergistic effect is observed.
Figure 4:
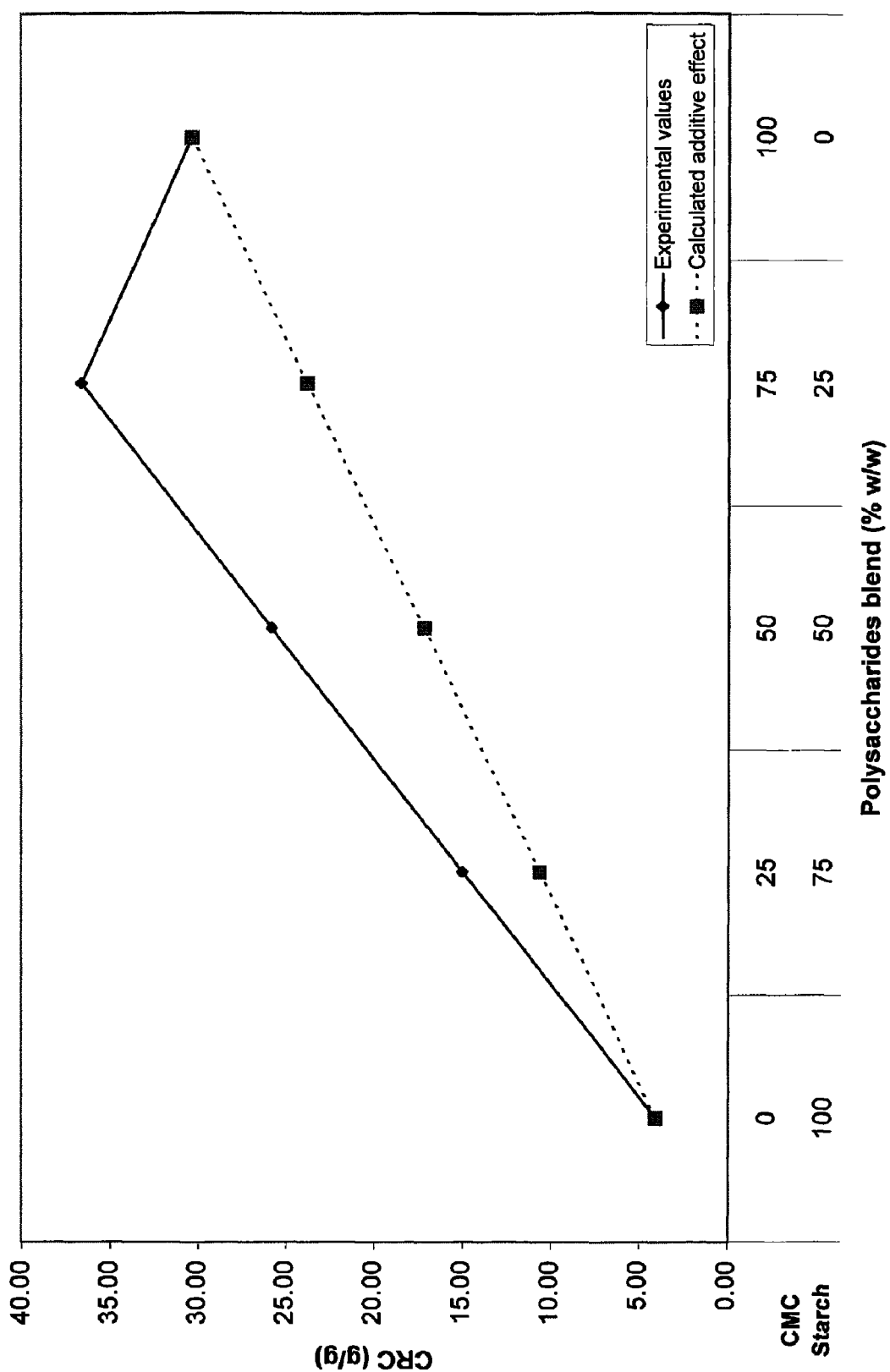
FIG. 4 shows a comparison between measured CRC values and calculated additive values in 0.9% NaCl solution for different ratios of CMC and starch. A strong synergistic effect is observed when higher values are obtained as compared to the corresponding calculated additive values.
Figure 5:
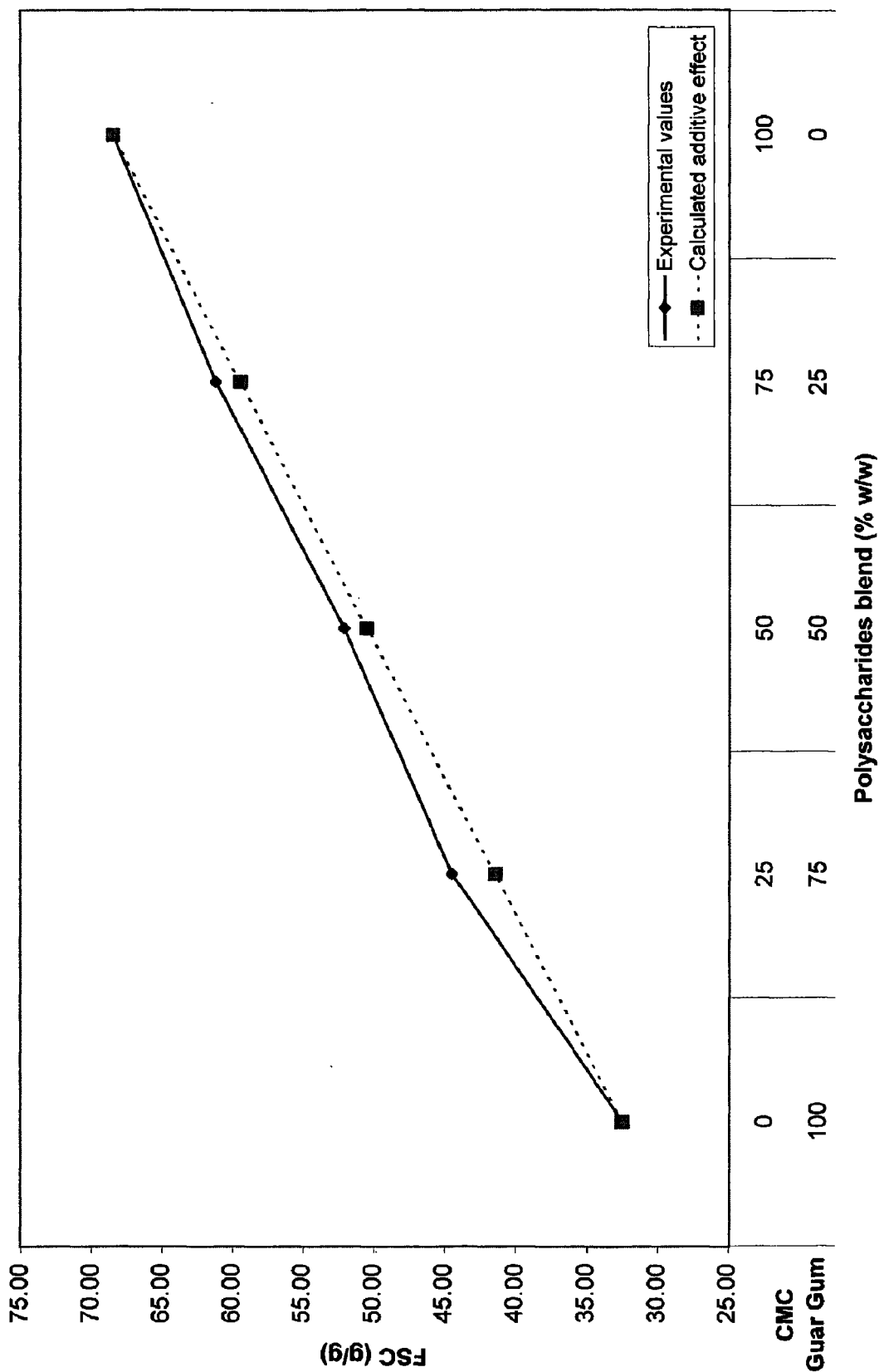
FIG. 5 shows a comparison between measured FSC values and calculated additive values in 0.9% NaCl solution for different ratios of CMC and guar gum. A weak synergistic effect is observed when higher values are obtained as compared to the corresponding calculated additive values.
Figure 6:
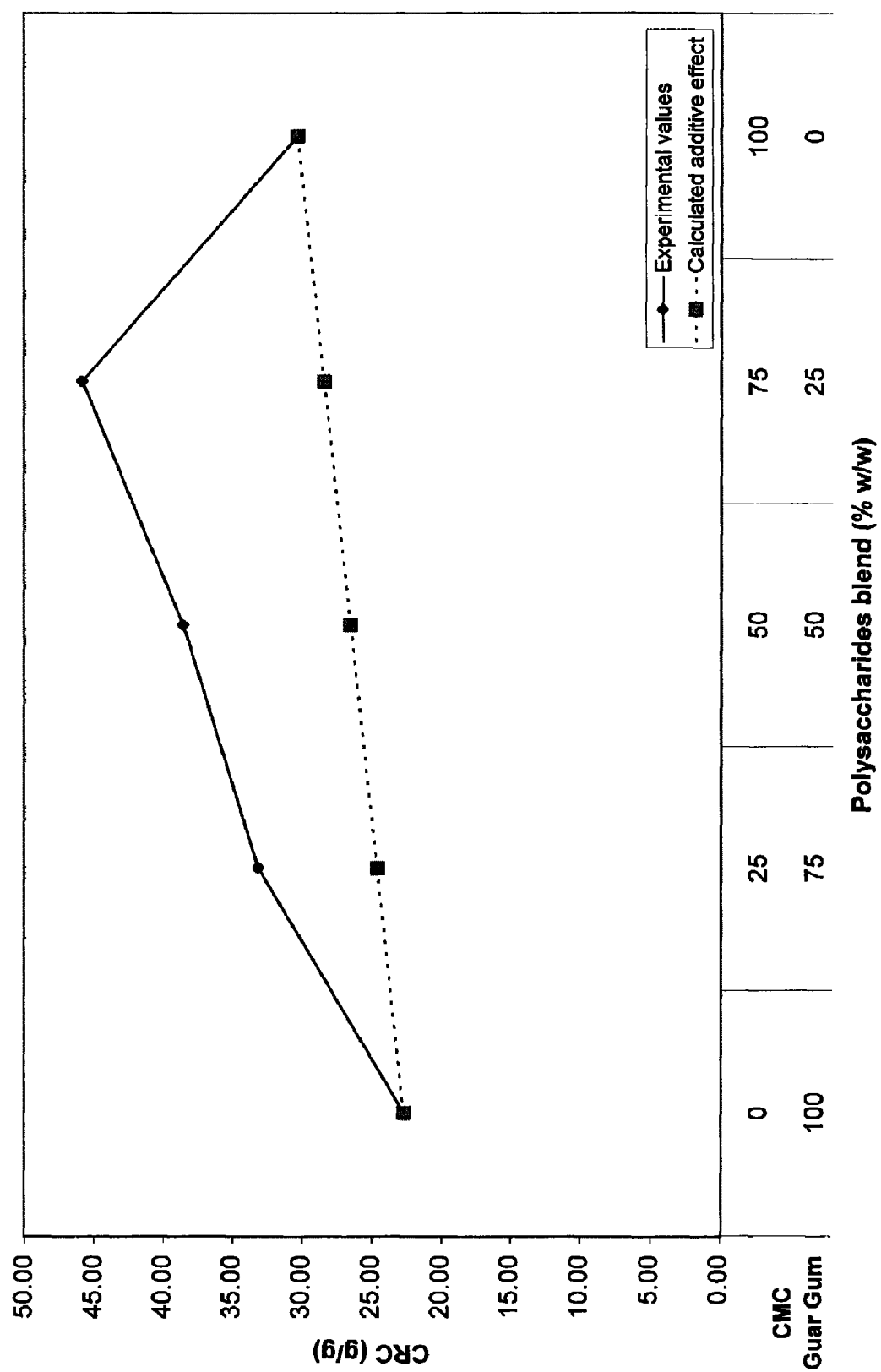
FIG. 6 shows a comparison between measured CRC values and calculated additive values in 0.9% NaCl solution for different ratios of CMC and guar gum. A strong synergistic effect is observed when higher values are obtained as compared to the corresponding calculated additive values.

A slight but significant synergistic effect can be observed on the FSC and CRC for two component blends including Guar gum and Starch (Table I, FIGS. 1 and 2). No synergistic effect on the FSC is observed for blends containing CMC and Starch. However these blends exhibit a strong synergistic effect on the CRC (Table I, FIGS. 3 and 4). A slight but significant synergistic effect on the FSC, is also observed for blends containing CMC and Guar gum (Table I, FIG. 5). However, these blends exhibit a strong synergistic effect on the CRC (Table I, FIG. 6).

As demonstrated, an AUL, FSC or CRC can be observed in two-component compositions, but rarely simultaneously for each measurement. In order to observe a synergistic effect on all the measurements, three or more component blends must be used. These multi-component blends preferably contain a component from each of the three classes described hereinabove.

Figure 7:
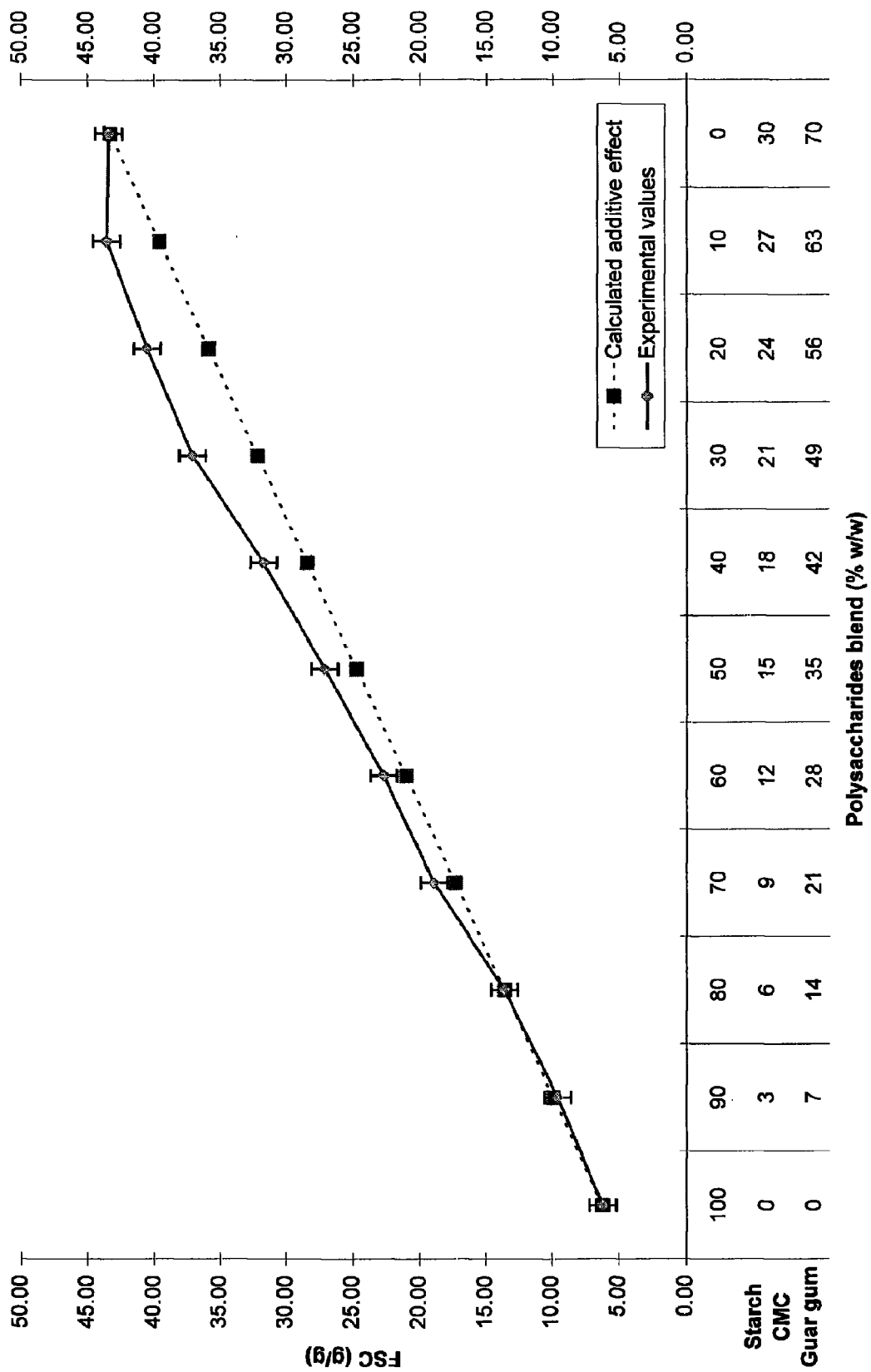
FIG. 7 shows a comparison between measured FSC values and calculated additive values in 0.9% NaCl solution for different ratios of starch, CMC and guar gum. A synergistic effect is observed when higher values are obtained as compared to the corresponding calculated additive values.

Polysaccharide three-component blends containing 0-70% Starch, 9-30% CMC, and 21-70% Guar Gum, and preferably between 10-60% Starch, 12-27% CMC, and 28-63% Guar Gum demonstrate a strong synergistic effect by increasing values of FSC up to 44 g/g with a synergistic effect near 5 g/g (Table II, FIG. 7).

Figure 8:
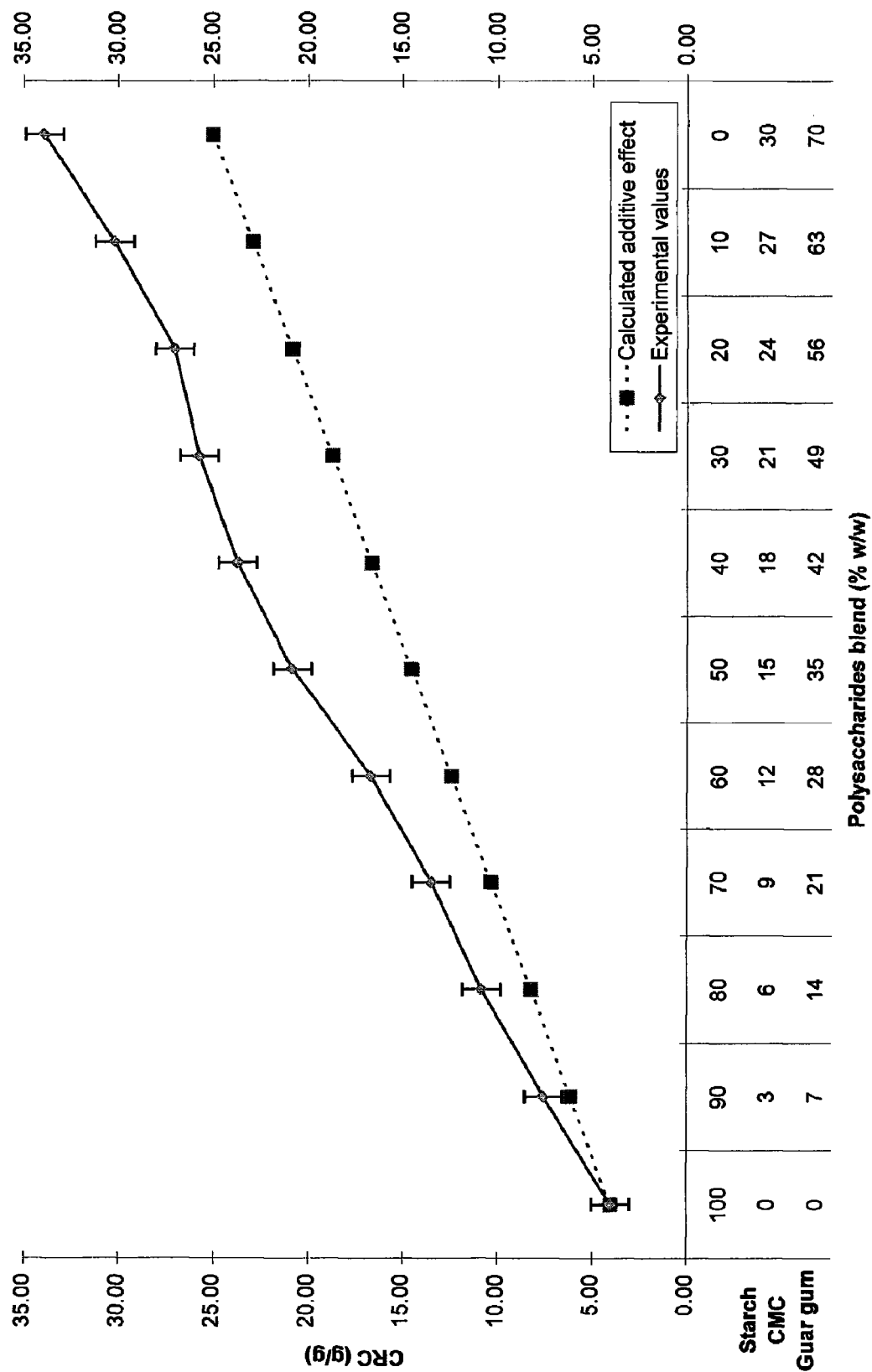
FIG. 8 shows a comparison between measured CRC values and calculated additive values in 0.9% NaCl solution for different ratios of starch, CMC and guar gum. A synergistic effect is observed when higher values are obtained as compared to the corresponding calculated additive values. The figure also shows a synergistic effect in the absence of starch.

Similarly, polysaccharide three-component blends or mixtures containing 0-70% Starch, 9-30% CMC, and 21-70% Guar Gum, and preferably between 10-60% Starch, 12-27% CMC, and 28-63% Guar Gum demonstrate a synergistic effect by increasing values of CRC up to 34 g/g with a synergistic effect near 9 g/g (Table II, FIG. 8).

Figure 9:
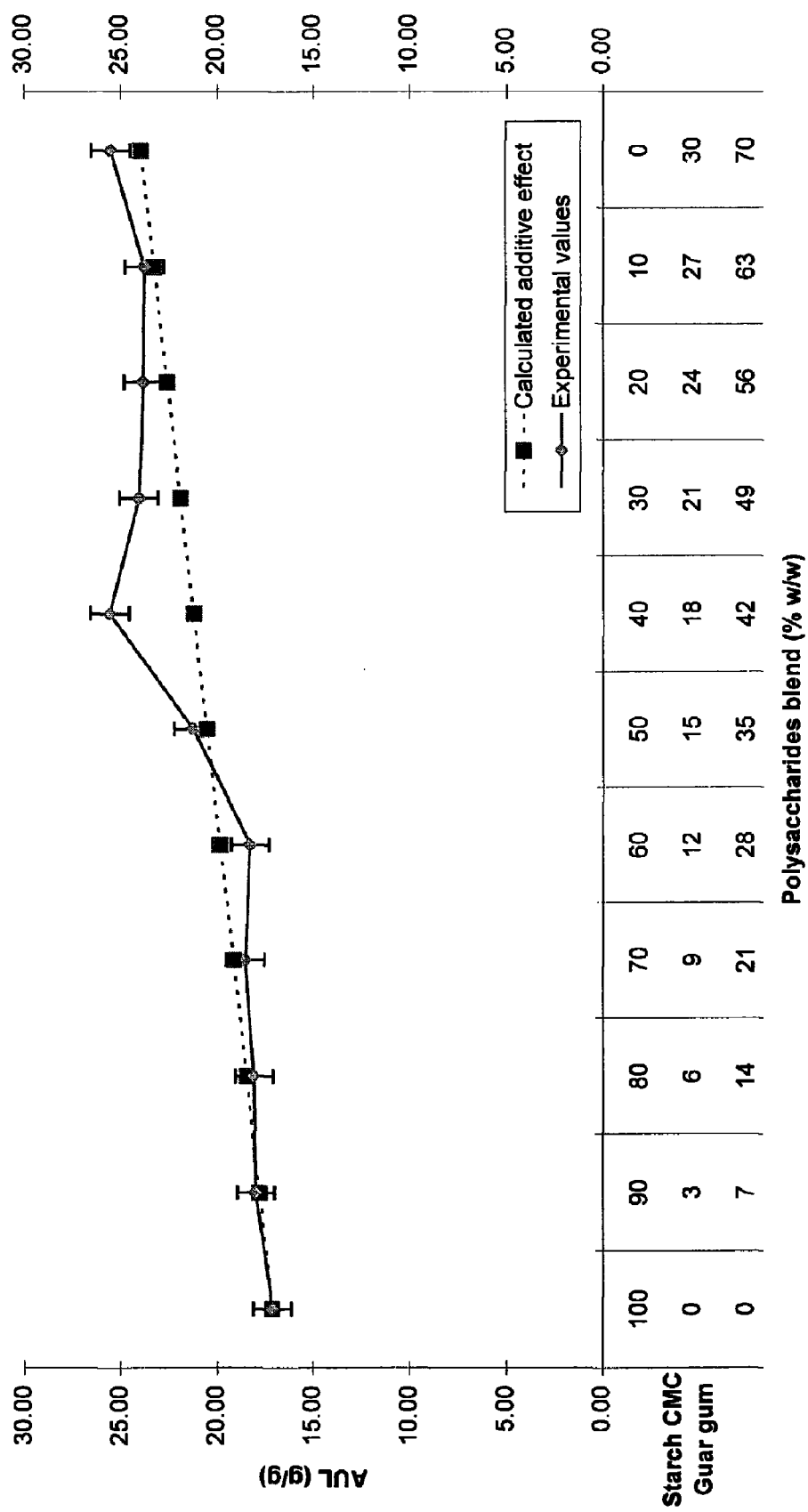
FIG. 9 shows a comparison between measured AUL values and calculated additive values in 0.9% NaCl solution for different ratios of starch, CMC and guar gum. A synergistic effect is observed when higher values are obtained as compared to the corresponding calculated additive values.

Similarly, polysaccharide three-component blends or mixtures containing 0-70% Starch, 9-30% CMC, and 21-70% Guar Gum, and preferably between 10-60% Starch, 12-27% CMC, and 28-63% Guar Gum demonstrate a synergistic effect by increasing values of AUL up to 25 g/g with a synergistic effect near 5 g/g (Table II, FIG. 9).

Figure 10:
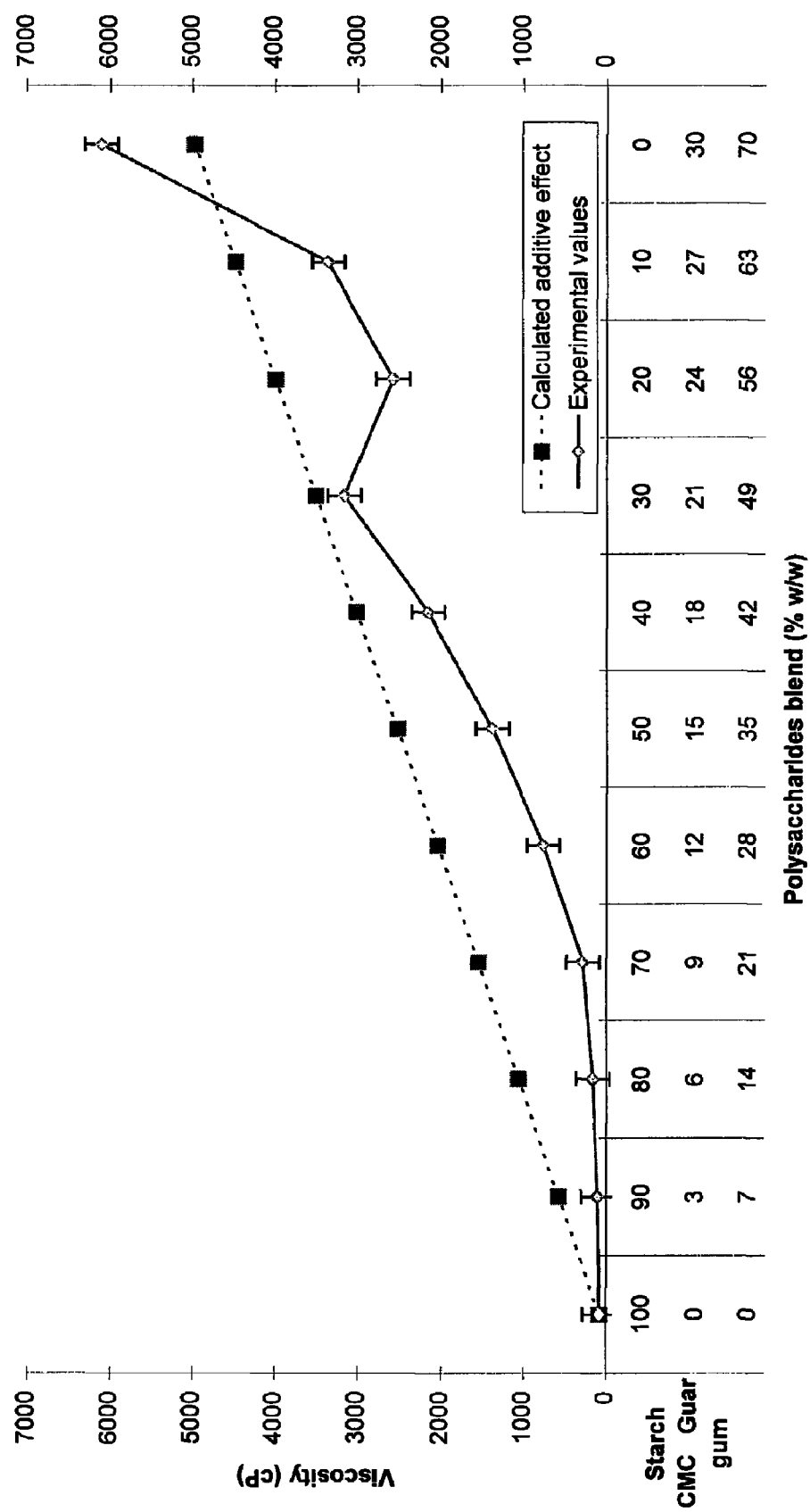
FIG. 10 shows a comparison between measured viscosity values and calculated additive values in 0.9% NaCl solution for different ratios of starch, CMC and guar gum. No synergistic effects are observed.

A synergistic effect on the viscosity was not observed (Table II, FIG. 10).

Examples 51 to 57 illustrate the use of gelling proteins and polypeptides such as gelatin and calcium caseinates, added to the complex synergistic polysaccharides formulations.

The use of other natural polysaccharides or gelling proteins in the composition of the present invention leads to significant synergistic effects as illustrated in Examples 29 to 50 (Tables III to VII). These results illustrate synergistic compositions with performances comparable to those obtained with synthetic superabsorbent polymers such as polyacrylates and polyacrylamides.

The present invention is illustrated in further detail by the following non-limiting examples.

Starting Materials

Pre-gelatinized wheat starch A (ADM-Ogilvie), sodium carboxymethyl cellulose (CMC aqualon; Hercules) and crude unmodified guar gum (L.V. Lomas Ltd.) have been used as starting materials for examples 1 to 28.

Modified starches such as carboxymethylstarch and esterified starches crosslinked with triglycoldichloride were provided by Lysac Technologies Inc.

Crude unmodified guar gum (Starlight), crude unmodified konjac gum (LIMAO Agricultural products), CMC aqualon (Hercules), xanthan gum (ADM), sodium alginate (Tic Gums), carrageenan (CP Kelco), pectin LM (Tic Gum) and chitosan Chito Clear (Primex) have been used as starting materials for examples 29 to 57.

AUL Measurements

The Absorption Under load (AUL) in a 0.9% NaCl solution at 0.3 psi was determined according to the recommended test method 442.1-99 from EDANA[2], using 0.1 gram of the absorbent in the apparatus.

FSC and CRC Measurements (Using Tea Bags)

Tea bags (10×10 cm) were made from heat sealable Ahlstrom filter paper 16.5±10.5 g/m2.

FSC Measurements

The Free Swell Capacity (FSC) in a 0.9% NaCl solution was determined according to the recommended test method 440.1-99 from EDANA.[3]

CRC Measurements

The Centrifuge Retention Capacity (CRC) in a 0.9% NaCl solution was determined according to the recommended test method 441.1-99 from EDANA.[4]

Viscosity Measurements

The viscosity was measured with a Brookfield RV DV II+viscometer at 50 RPM with a spindle No 6, using a 2% (W/W) solution made with a 0.9% NaCl solution and agitated for one hour before measurement.

Gel Strength Measurements

The gel strength was measured using a TA.XT2i from Texture Technologies with a cylindrical probe TA-12, load capacity 5 Kg, gain trigger 0.5 g, displacement 10 mm, time 5 seconds, speed 2.0 mm/second. The gel strength is expressed in force (g).

Biodegradability and Ecological Impact

According to the United States Environmental Protection Agency (EPA), the Zahn-Wellens test is useful for testing the biodegradability of a substance soluble in water to at least 50 mg of dissolved organic carbon (DOC) per liter (US Environmental Protection Agency (EPA), Fate, Transport and Transformation Test Guidelines, OPPTS 832.3200, Zahn-Wellens/ EMPA test, EPA712-C-98-084, January 1998).[5] For substances that are not completely soluble, it offers only a qualitative indication of whether these substances are basically susceptible to biological degradation or not (Buchholz et al., U.S. Pat. No. 5,789,570). An activated sludge was used in Example 27 to evaluate the biodegradability. A technicon carbon analyzer was used to measure the DOC and the percentage biodegradability was calculated according to the DOC obtained, and reported in the equation given in reference 4. Example 27 showed no toxicity for microorganisms and no toxic product was detected that would destroy the aquatic fauna, particularly the micro crustacean Daphnia magna. Mineral medium was used as a blank and the positive control was ethylene glycol, which showed 100% biodegradability after 14 days.

Composition Percentages

Composition percentages are all related in weight by weight (w/w) percentages.

Hypoallergenisity

Hypoallergenisity tests were performed by the Consumer Product Testing Co. according to the ASTM D6355-8 norm[6]; performed with adherence to ICH Guideline E6 for good clinical practice and requirements provided for in 21 CFR parts 50 and 56 in accordance to standard operating procedures and applicable protocols. The products have been tested with sixty (60) qualified subjects, male and female, ranging in age from 20 to 72 years.

The upper back, between the scapulae, served as the treatment area. Approximately 0.2 g of the material was applied to the ¾"×¾" absorbent pad portion of a saline moistened adhesive dressing. Patches were applied three times per week (e.g. Monday, Wednesday and Friday) for a total of nine (9) applications. The site was marked to ensure the continuity of patch application. Following supervised removal and scoring of the first induction patch, participants were instructed to remove all subsequent induction patches at home, twenty-four hours after application.

The following evaluation key was used by all participants:
0: No visible skin reaction;
+: Barely perceptible or spotty erytherma;
1: Mild erytherma covering most of the test site;
2: Moderate erytherma, possible presence of mild edema;
3: Marked erytherma, possible edema;
4: Severe erytherma, possible edema, vesiculation, bullae or ulceration.

EXAMPLES 1 TO 15

Synergy for FSC and CRC with Two Component Blends

Two component blends (examples 1 to 15) comprising Guar Gum and Starch, CMC and Starch, CMC and Guar Gum were prepared by weighing 0, 25, 50, 75 and 100% of each material. The blends were mixed vigorously in a 20 ml vial. The Free Swell Capacity (FSC) and Centrifuge Retention Capacity (CRC) was measured for each of the two component blends, and was subsequently compared with calculated additive values based on component performances. The results are illustrated in Table I, as well as in FIGS. 1 to 6.

TABLE I

Examples for two-component blends

| | Blends | | | Measured | | Calculated | | Synergy | |
|---|---|---|---|---|---|---|---|---|---|
| Example | Guar Gum % | CMC B315 % | Starch % | FSC g/g | CRC g/g | FSC g/g | CRC g/g | FSC g/g | CRC g/g |
| 1 | 100 | 0 | | 32.48 | 22.72 | 32.48 | 22.72 | 0.00 | 0.00 |
| 2 | 75 | 25 | | 44.50 | 33.17 | 41.49 | 24.64 | 3.02 | 8.54 |
| 3 | 50 | 50 | | 52.10 | 38.61 | 50.49 | 26.55 | 1.61 | 12.06 |
| 4 | 25 | 75 | | 61.20 | 45.89 | 59.50 | 28.47 | 1.71 | 17.43 |
| 5 | 0 | 100 | | 68.50 | 30.38 | 68.50 | 30.38 | 0.00 | 0.00 |
| 6 | 0 | | 100 | 6.20 | 4.04 | 6.20 | 4.04 | 0.00 | 0.00 |
| 7 | 25 | | 75 | 14.00 | 10.46 | 12.77 | 8.71 | 1.23 | 1.75 |
| 8 | 50 | | 50 | 20.65 | 13.48 | 19.34 | 13.38 | 1.31 | 0.10 |
| 9 | 75 | | 25 | 26.10 | 18.03 | 25.91 | 18.05 | 0.19 | −0.02 |
| 10 | 100 | | 0 | 32.48 | 22.72 | 32.48 | 22.72 | 0.00 | 0.00 |
| 11 | | 0 | 100 | 6.20 | 4.04 | 6.20 | 4.04 | 0.00 | 0.00 |
| 12 | | 25 | 75 | 20.41 | 15.01 | 21.78 | 10.63 | −1.37 | 4.39 |
| 13 | | 50 | 50 | 34.55 | 25.84 | 37.35 | 17.21 | −2.80 | 8.63 |
| 14 | | 75 | 25 | 52.44 | 36.64 | 52.93 | 23.80 | −0.48 | 12.85 |
| 15 | | 100 | 0 | 68.50 | 30.38 | 68.50 | 30.38 | 0.00 | 0.00 |

Components performances

| | Measured | |
|---|---|---|
| | FSC g/g | CRC g/g |
| Starch 2604 | 6.20 | 4.04 |
| Guar Gum | 32.48 | 22.72 |
| CMC Aqualon B315 | 68.50 | 30.38 |

EXAMPLES 16 TO 26

Synergy for FSC, CRC, AUL and Viscosity with Three Component Blends

Three component blends (examples 16 to 26) were prepared by weighing 0 to 100% of Starch, 0 to 30% of CMC and 0 to 70% of Guar Gum. The blends were mixed vigorously in a 20 ml vial. The FSC, CRC, Absorption under load (AUL) and viscosity was measured for each of the three component blends, and was subsequently compared with calculated additive values based on component performances. The results are illustrated in Table II, as well as in FIGS. 7 to 10.

TABLE II

Examples for a three-component blend

| | Blends | | | Measured | | | | Calculated | | | | Synergy | | | |
|---|---|---|---|---|---|---|---|---|---|---|---|---|---|---|---|
| Example | Guar Gum % | CMC B315 % | Starch % | FSC g/g | CRC g/g | AUL g/g | Visc. cP | FSC g/g | CRC g/g | AUL g/g | Visc. cP | FSC g/g | CRC g/g | AUL g/g | Visc. cP |
| 16 | 0 | 0 | 100 | 6.20 | 4.04 | 17.09 | 80 | 6.20 | 4.04 | 17.09 | 80 | 0.00 | 0.00 | 0.00 | 0 |
| 17 | 7 | 3 | 90 | 9.57 | 7.55 | 17.98 | 100 | 9.91 | 6.14 | 17.78 | 569 | −0.34 | 1.41 | 0.20 | −469 |
| 18 | 14 | 6 | 80 | 13.62 | 10.83 | 18.07 | 160 | 13.62 | 8.24 | 18.46 | 1059 | 0.00 | 2.59 | −0.39 | −899 |
| 19 | 21 | 9 | 70 | 18.94 | 13.50 | 18.54 | 280 | 17.33 | 10.33 | 19.15 | 1548 | 1.61 | 3.17 | −0.61 | −1268 |
| 20 | 28 | 12 | 60 | 22.70 | 16.67 | 18.28 | 760 | 21.03 | 12.43 | 19.84 | 2038 | 1.67 | 4.24 | −1.56 | −1278 |
| 21 | 35 | 15 | 50 | 27.12 | 20.83 | 21.23 | 1380 | 24.74 | 14.53 | 20.53 | 2527 | 2.38 | 6.30 | 0.70 | −1147 |
| 22 | 42 | 18 | 40 | 31.72 | 23.72 | 25.57 | 2160 | 28.45 | 16.63 | 21.21 | 3016 | 3.27 | 7.09 | 4.36 | −856 |
| 23 | 49 | 21 | 30 | 37.08 | 25.73 | 24.05 | 3160 | 32.16 | 18.72 | 21.90 | 3506 | 4.92 | 7.01 | 2.15 | −346 |
| 24 | 56 | 24 | 20 | 40.51 | 27.02 | 23.83 | 2580 | 35.87 | 20.82 | 22.59 | 3995 | 4.64 | 6.20 | 1.24 | −1415 |
| 25 | 63 | 27 | 10 | 43.56 | 30.17 | 23.79 | 3360 | 39.58 | 22.92 | 23.28 | 4485 | 3.98 | 7.25 | 0.51 | −1125 |
| 26 | 70 | 30 | 0 | 43.38 | 33.88 | 25.50 | 6100 | 43.29 | 25.02 | 23.96 | 4974 | 0.09 | 8.86 | 1.54 | 1126 |

Component performances

| | Measured | | | |
|---|---|---|---|---|
| | FSC g/g | CRC g/g | AUL g/g | Visc. cP |
| Starch 2604 | 6.20 | 4.04 | 17.09 | 80 |
| Guar Gum | 32.48 | 22.72 | 20.96 | 420 |
| CMC Aqualon B315 | 68.50 | 30.38 | 30.97 | 15600 |

EXAMPLE 27

Biodegradability, Hypoallergenisity, FSC, CRC and AUL of Three Component Blend Pregelatinized Wheat Starch (15 Kg, 50%, 30-170 mesh (147 to 589 microns)); CMC (3.9 Kg, 13%, 30-170 mesh (147 to 589 microns)); and guar gum (11.1 Kg, 37%, 30-170 mesh (147 to 589 microns)) were vigorously mixed in a double action mixer (LELAND 100 DA-70, 40 Kg capacity) over a period of 15 minutes.

FSC=29.0 g/g
CRC=20.3 g/g
AUL=20.0 g/g
Biodegradability: 91.1% after 28 days.

Hypoallerginicity: Panel No. 20020142, No visible skin reaction (0) for all sixty (60) qualified subjects, on all nine (9) applications.

EXAMPLE 28

Effects on the FSC, CRC, AUL, GEL Strength and Viscosity of Ionic Polysaccharides Having Different Viscosities Pregelatinized Wheat Starch (1000 Kg, 44.67% (ADM)); Guar Gum Procol (900 Kg, 40.21% (LV Lomas)); CMC Aqualon (114 Kg, 5.07% (Hercules)); CMC Gabrosa (125 Kg, 5.58% (Akzo Nobel)); and CMC (100 Kg, 4.47% (Amtex)) were mixed in an industrial mixer for 10 minutes.

FSC=27.47 g/g
CRC=23.53 g/g
AUL=21.69 g/g
Gel strength=25.01 g
Viscosity=2180 Centipoises (Cp)

EXAMPLES 29 TO 32

Effect on the FSC, CRC and AUL of Three-Component Blends, of Different Starch Based Products Four different starch based products (44.67%) were mixed with Guar Gum (40.21%) and CMC (15.12%) as described in Examples 1 to 15. The different starch based products used were pregelatinized wheat starch (ADM), sodium carboxymethyl wheat starch crosslinked with triglycol dichloride (Lysac Technologies Inc.), sodium maleate wheat starch crosslinked with triglycol dichloride (Lysac Technologies Inc.), and a hybrid of the latter two (Lysac Technologies Inc.). The results are illustrated in Table III.

TABLE III

Examples for a three-component blend with different starch based product, guar gum and CMC

| | Blends | | | | Measured | | | Calculated | | | Synergy | | |
| | Guar | CMC | | | | | | | | | | | |
| Example | Gum % | B315 % | % | Starch type | FSC g/g | CRC g/g | AUL g/g | FSC g/g | CRC g/g | AUL g/g | FSC g/g | CRC g/g | AUL g/g |
| --- | --- | --- | --- | --- | --- | --- | --- | --- | --- | --- | --- | --- | --- |
| 29 | 40.21 | 15.12 | 44.67 | 1 | 35.71 | 33.13 | 27.2 | 30.26 | 26.06 | 18.36 | 5.35 | 7.07 | 8.84 |
| 30 | 40.21 | 15.12 | 44.67 | 2 | 47.88 | 43.51 | 30.50 | 39.96 | 32.45 | 26.95 | 7.92 | 11.06 | 3.55 |
| 31 | 40.21 | 15.12 | 44.67 | 3 | 38.33 | 35.38 | 26.26 | 36.39 | 28.43 | 26.10 | 1.94 | 6.95 | 0.16 |
| 32 | 40.21 | 15.12 | 44.67 | 4 | 38.31 | 34.64 | 32.04 | 36.39 | 29.32 | 23.57 | 1.92 | 5.32 | 8.47 |

Component performances

| | Measured | | |
| | FSC g/g | CRC g/g | AUL g/g |
| --- | --- | --- | --- |
| Starch type 1: Pregel 2604 (ADM) | 6.50 | 4.70 | 11.47 |
| Starch type 2: Carboxymethyl crosslinked with TEG | 28.00 | 19.00 | 30.70 |
| Starch type 3: Maleate crosslinked with TEG | 20.00 | 10.00 | 28.81 |
| Starch type 4: Hybrid crosslinked with TEG | 20.00 | 12.00 | 23.14 |
| Guar Gum (Starlight) | 48.73 | 45.68 | 22.60 |
| CMC Aqualon B315 | 52.00 | 37.00 | 27.41 |

EXAMPLES 33 TO 36

Effect on the FSC, CRC and AUL of Three-Component Blends, of Different Starch Based Products Four different starch based products (44.67%) were mixed with Konjac Gum (40.21%) and CMC (15.12%) as described in Examples 1 to 15. The different starch based products used were pregelatinized wheat starch (ADM), sodium carboxymethyl wheat starch crosslinked with triglycol dichloride (Lysac Technologies Inc.), sodium maleate wheat starch crosslinked with triglycol dichloride (Lysac Technologies Inc.) and a hybrid of the latter two (Lysac Technologies Inc.). The results are illustrated in Table VI.

TABLE IV

Examples for a three-component blend with different starch based product, konjac gum and CMC

| | Blends | | | | Measured | | | Calculated | | | Synergy | | |
|---|---|---|---|---|---|---|---|---|---|---|---|---|---|
| | | CMC | | | | | | | | | | | |
| Example | Konjac % | B315 % | Starch % | Starch type | FSC g/g | CRC g/g | AUL g/g | FSC g/g | CRC g/g | AUL g/g | FSC g/g | CRC g/g | AUL g/g |
| 33 | 40.21 | 15.12 | 44.67 | 1 | 32.99 | 29.55 | 21.84 | 29.56 | 25.34 | 17.16 | 3.43 | 4.21 | 4.68 |
| 34 | 40.21 | 15.12 | 44.67 | 2 | 39.75 | 36.92 | 22.21 | 39.16 | 31.73 | 25.75 | 0.59 | 5.19 | −3.54 |
| 35 | 40.21 | 15.12 | 44.67 | 3 | 33.98 | 31.33 | 32.20 | 35.59 | 27.71 | 24.90 | −1.61 | 3.62 | 7.30 |
| 36 | 40.21 | 15.12 | 44.67 | 4 | 34.32 | 31.07 | 27.14 | 35.59 | 28.60 | 22.37 | −1.27 | 2.47 | 4.77 |

Component performances

| | Measured | | |
|---|---|---|---|
| | FSC g/g | CRC g/g | AUL g/g |
| Starch type 1: Pregel 2604 (ADM) | 6.50 | 4.70 | 11.47 |
| Starch type 2: Carboxymethyl crosslinked with TEG | 28.00 | 19.00 | 30.70 |
| Starch type 3: Maleate crosslinked with TEG | 20.00 | 10.00 | 28.81 |
| Starch type 4: Hybrid crosslinked with TEG | 20.00 | 12.00 | 23.14 |
| Konjac Gum (LIMAO) | 46.73 | 43.89 | 19.62 |
| CMC Aqualon B315 | 52.00 | 37.00 | 27.41 |

EXAMPLES 37 TO 40

Effect on the FSC, CRC and AUL of Three-Component Blends, of Different Starch Based Products Four different starch based products (44.67%) were mixed with Guar Gum (40.21%) and sodium Alginate (15.12%) as described in Examples 1 to 15. The different starch based products used were pregelatinized wheat starch (ADM), sodium carboxymethyl wheat starch crosslinked with triglycol dichloride (Lysac Technologies Inc.), sodium maleate wheat starch crosslinked with triglycol dichloride (Lysac Technologies Inc.) and a hybrid of the latter two (Lysac Technologies Inc.). The results are illustrated in Table V.

TABLE V

Examples for a three-component blend with different starch based product, guar gum and sodium alginate

| | Blends | | | | Measured | | | Calculated | | | Synergy | | |
|---|---|---|---|---|---|---|---|---|---|---|---|---|---|
| Example | Guar % | Alginate % | Starch % | Starch type | FSC g/g | CRC g/g | AUL g/g | FSC g/g | CRC g/g | AUL g/g | FSC g/g | CRC g/g | AUL g/g |
| 37 | 40.21 | 15.12 | 44.67 | 1 | 35.88 | 33.12 | 21.42 | 29.70 | 24.15 | 18.25 | 6.18 | 8.97 | 3.17 |
| 38 | 40.21 | 15.12 | 44.67 | 2 | 46.95 | 40.06 | 26.23 | 39.30 | 30.54 | 26.84 | 7.65 | 9.52 | −0.61 |
| 39 | 40.21 | 15.12 | 44.67 | 3 | 39.40 | 33.51 | 28.69 | 35.73 | 26.52 | 26.00 | 3.67 | 6.99 | 2.69 |
| 40 | 40.21 | 15.12 | 44.67 | 4 | 36.85 | 31.60 | 31.80 | 35.73 | 27.41 | 23.47 | 1.12 | 4.19 | 8.33 |

Component performances

| | Measured | | |
|---|---|---|---|
| | FSC g/g | CRC g/g | AUL g/g |
| Starch type 1: Pregel 2604 (ADM) | 6.50 | 4.70 | 11.47 |
| Starch type 2: Carboxymethyl crosslinked with TEG | 28.00 | 19.00 | 30.70 |
| Starch type 3: Maleate crosslinked with TEG | 20.00 | 10.00 | 28.81 |
| Starch type 4: Hybrid crosslinked with TEG | 20.00 | 12.00 | 23.14 |
| Sodium alginate (Tic Gums) | 45.02 | 33.88 | 26.14 |
| Guar gum (Starlight) | 48.73 | 45.68 | 22.60 |

EXAMPLES 41 TO 44

Effects on the FSC, CRC and AUL of Three-Component Blends, of Different Starch Based Products Four different starch based products (44.67%) were mixed with Guar Gum (40.21%) and Konjac Gum (15.12%) as described in Examples 1 to 15. The different starch based products used were pregelatinized wheat starch (ADM), sodium carboxymethyl wheat starch crosslinked with triglycol dichloride (Lysac Technologies Inc.), sodium maleate wheat starch crosslinked with triglycol dichloride (Lysac Technologies Inc.) and a hybrid of the latter two (Lysac Technologies Inc.). The results are illustrated in Table VI.

TABLE VI

Examples for a three-component blend with different starch based product, guar and konjac gum

| | Blends | | | | Measured | | | Calculated | | | Synergy | | |
|---|---|---|---|---|---|---|---|---|---|---|---|---|---|
| Example | Starch % | Guar % | Konjac % | Starch type | FSC g/g | CRC g/g | AUL g/g | FSC g/g | CRC g/g | AUL g/g | FSC g/g | CRC g/g | AUL g/g |
| 41 | 40.21 | 15.12 | 44.67 | 1 | 32.49 | 30.42 | 27.26 | 29.56 | 27.10 | 17.18 | 2.93 | 3.32 | 10.08 |
| 42 | 40.21 | 15.12 | 44.67 | 2 | 43.27 | 40.25 | 27.20 | 39.17 | 33.49 | 25.77 | 4.10 | 6.76 | 1.43 |
| 43 | 40.21 | 15.12 | 44.67 | 3 | 36.55 | 34.06 | 31.96 | 35.59 | 29.47 | 24.92 | 0.96 | 4.59 | 7.04 |
| 44 | 40.21 | 15.12 | 44.67 | 4 | 37.02 | 33.95 | 31.96 | 35.59 | 30.36 | 22.39 | 1.43 | 3.59 | 9.57 |

Component performances

| | Measured | | |
|---|---|---|---|
| | FSC g/g | CRC g/g | AUL g/g |
| Starch type 1: Pregel 2604 (ADM) | 6.50 | 4.70 | 11.47 |
| Starch type 2: Carboxymethyl crosslinked with TEG | 28.00 | 19.00 | 30.70 |
| Starch type 3: Maleate crosslinked with TEG | 20.00 | 10.00 | 28.81 |
| Starch type 4: Hybrid crosslinked with TEG | 20.00 | 12.00 | 23.14 |
| Guar gum (Starlight) | 48.73 | 45.68 | 22.60 |
| Konjac gum (LIMAO) | 46.73 | 43.89 | 19.62 |

EXAMPLES 45 TO 50

Effect on the FSC, CRC and AUL of Multi-Component Blends, of Different Polysaccharides Blends were prepared by mixing pregelatinized wheat starch (ADM), as the first component class (starch based product), guar gum (Starlight) and konjac gum (LIMAO) as the second component class (polygalactomanan and polyglucomanan) and finally, CMC (Hercules), xanthan (ADM), sodium alginate (Tic Gums), carrageenan (CP Kelco), pectine (Tic Gums) and chitosan (Primex) as the third component class (ionic class) as described in Example 1 to 15. The synergistic results on the FSC, CRC and AUL are illustrated in Table VII.

TABLE VII

Examples for multi-component blends

| | Blends | | | | | | | | Measured | | | Calculated | | | Synergy | | |
|---|---|---|---|---|---|---|---|---|---|---|---|---|---|---|---|---|---|
| Ex. | Starch % | Guar % | Konjac % | CMC % | Xanthan % | Alginate % | Carrageenan % | Pectine % | FSC g/g | CRC g/g | AUL g/g | FSC g/g | CRC g/g | AUL g/g | FSC g/g | CRC g/g | AUL g/g |
| 45 | 40.00 | 30.00 | 0.00 | 20.00 | 0.00 | 10.00 | 0.00 | 0.00 | 32.89 | 29.38 | 23.41 | 32.38 | 25.42 | 19.52 | 0.51 | 3.96 | 3.89 |
| 46 | 30.00 | 37.50 | 0.00 | 22.50 | 0.00 | 10.00 | 0.00 | 0.00 | 38.13 | 34.00 | 23.48 | 36.69 | 29.30 | 20.76 | 1.44 | 4.70 | 2.72 |
| 47 | 30.00 | 20.00 | 20.00 | 10.00 | 10.00 | 0.00 | 10.00 | 0.00 | 41.30 | 38.83 | 20.76 | 38.99 | 33.11 | 19.66 | 2.31 | 5.72 | 1.10 |
| 48 | 30.00 | 20.00 | 20.00 | 10.00 | 10.00 | 0.00 | 0.00 | 10.00 | 38.86 | 35.30 | 19.00 | 38.59 | 32.73 | 18.54 | 0.27 | 2.57 | 0.46 |
| 49 | 30.00 | 20.00 | 20.00 | 10.00 | 0.00 | 0.00 | 10.00 | 10.00 | 42.39 | 38.88 | 21.73 | 34.85 | 29.42 | 18.73 | 7.54 | 9.46 | 2.99 |
| 50 | 30.00 | 20.00 | 20.00 | 10.00 | 0.00 | 10.00 | 0.0 | 10.00 | 36.51 | 32.28 | 25.10 | 35.11 | 28.47 | 18.79 | 1.40 | 3.81 | 6.31 |

TABLE VII-continued

| | Component performances | | |
|---|---|---|---|
| | Measured | | |
| | FSC g/g | CRC g/g | AUL g/g |
| Starch 2604 (ADM) | 6.50 | 4.70 | 11.47 |
| Guar gum (Starlight) | 48.73 | 45.68 | 22.60 |
| Konjac gum (LIMAO) | 46.73 | 43.89 | 19.62 |
| CMC (Aqualon B315) | 58.20 | 45.90 | 27.41 |
| Sodium Alginate (Tic Gums) | 47.63 | 24.35 | 26.73 |
| Carrageenan (CP Kelko) | 45.02 | 33.88 | 26.14 |
| Pectine (Tic Gums) | 41.02 | 30.06 | 14.95 |
| Xanthan (ADM) | 82.46 | 67.02 | 24.20 |
| Chitosan (Primex) | 8.18 | 1.63 | 16.14 |

EXAMPLES 51 TO 57

Effect on the FSC, CRC and AUL of Multi-Component Blends, of Different Polysaccharides with the Presence of Proteins Blends were prepared by mixing gelling proteins such as gelatin and calcium caseinate with pregelatinized wheat starch (ADM), as the first component class (modified starch), guar gum (Starlight) and konjac gum (LIMAO) as the second components class (polygalactomanan and polyglucomanan) and finally, CMC (Hercules), xanthan (ADM), sodium alginate (Tic Gums), carrageenan (CP Kelco), pectine (Tic Gums) and chitosan (Primex) as the third components class (ionic class) as described in Examples 1 to 15. The synergistic results on the FSC, CRC and AUL are illustrated in Table VIII.

TABLE VIII

Examples for multi-component blends with proteins

| Ex. | Starch % | Guar % | Konjac % | CMC % | Xanthan % | Alginate % | Carra-geenan % | Pectine % | Chitosan % | Gelatin % | Casein % |
|---|---|---|---|---|---|---|---|---|---|---|---|
| 51 | 50.00 | 0.00 | 0.00 | 0.00 | 0.00 | 14.50 | 14.50 | 14.50 | 1.50 | 0.00 | 5.00 |
| 52 | 50.00 | 16.00 | 0.00 | 0.00 | 0.00 | 14.50 | 14.50 | 0.00 | 0.00 | 0.00 | 5.00 |
| 53 | 50.00 | 16.00 | 0.00 | 0.00 | 0.00 | 14.50 | 14.50 | 0.00 | 0.00 | 5.00 | 0.00 |
| 54 | 35.00 | 50.00 | 0.00 | 0.00 | 0.00 | 0.00 | 0.00 | 0.00 | 0.00 | 15.00 | 0.00 |
| 55 | 55.00 | 10.00 | 17.00 | 5.00 | 2.00 | 0.00 | 5.00 | 0.00 | 0.00 | 5.00 | 1.00 |
| 56 | 45.00 | 26.00 | 5.00 | 5.00 | 5.00 | 2.00 | 2.00 | 2.00 | 0.00 | 6.00 | 2.00 |
| 57 | 35.00 | 50.00 | 0.00 | 0.00 | 0.00 | 5.00 | 0.00 | 0.00 | 0.00 | 5.00 | 5.00 |

| | Measured | | | Calculated | | | Synergy | | |
|---|---|---|---|---|---|---|---|---|---|
| Ex. | FSC g/g | CRC g/g | AUL g/g | FSC g/g | CRC g/g | AUL g/g | FSC g/g | CRC g/g | AUL g/g |
| 51 | 28.38 | 19.75 | 17.35 | 23.00 | 15.18 | 16.58 | 5.38 | 4.57 | 0.77 |
| 52 | 32.53 | 25.09 | 21.21 | 24.73 | 18.10 | 17.78 | 7.80 | 6.99 | 3.43 |
| 53 | 30.08 | 23.91 | 19.81 | 25.11 | 18.41 | 17.86 | 4.97 | 5.50 | 1.95 |
| 54 | 31.23 | 28.78 | 22.35 | 28.52 | 25.41 | 17.83 | 2.71 | 3.37 | 4.52 |
| 55 | 29.59 | 26.84 | 19.71 | 23.88 | 20.25 | 16.06 | 5.71 | 6.59 | 3.65 |
| 56 | 31.98 | 27.76 | 19.27 | 28.49 | 23.97 | 17.27 | 3.49 | 3.79 | 2.00 |
| 57 | 32.21 | 29.09 | 19.90 | 29.89 | 26.01 | 18.26 | 2.32 | 3.08 | 1.64 |

| | Component performances | | |
|---|---|---|---|
| | Measured | | |
| | FSC g/g | CRC g/g | AUL g/g |
| Starch 2604 (ADM) | 6.50 | 4.70 | 11.47 |
| Guar gum (Starlight) | 48.73 | 45.68 | 22.60 |
| Konjac gum (LIMAO) | 46.73 | 43.89 | 19.62 |
| CMC (Aqualon B315) | 58.20 | 45.90 | 27.41 |
| Sodium Alginate (Tic Gums) | 47.63 | 24.35 | 26.73 |
| Carrageenan (CP Kelko) | 45.02 | 33.88 | 26.14 |
| Pectine (Tic Gums) | 41.02 | 30.06 | 14.95 |
| Xanthan (ADM) | 82.46 | 67.02 | 24.20 |
| Chitosan (Primex) | 8.18 | 1.63 | 16.14 |
| Gelatin | 12.56 | 6.15 | 16.80 |
| Casein | 4.90 | 0.00 | 15.35 |

REFERENCES

1. Beenackers A. A. C. M. et al. An experimental study on the carboxymethylation of granular potato starch in non-aqueous media. Carbohydr. Polym., 1, 45, 219-226.
2. EDANA, Absorbency Against Pressure No. 442.1-99, Recommended Test Method: Superabsorbent materials-Polyacrylate superabsorbent powders-Absorbency Against Pressure by Gravimetric Determination, February 1999.
3. EDANA, Free Swell Capacity No. 440.1-99, Recommended test Method: Superabsorbent materials-Polyacrylate superabsorbent powders-Free Swell Capacity in Saline by Gravimetric Determination, February 1999.
4. EDANA, Centrifuge Retention Capacity No. 441.1-99, Recommended Test Method: Superabsorbent materials-Polyacrylate superabsorbent powders-Centrifuge Retention Capacity in Saline by Gravimetric Determination, February 1999.
5. US Environmental Protection Agency (EPA), Fate, Transport and Transformation Test Guidelines, OPPTS 832.3200, Zahn-Wellens/EMPA test, EPA712-C-98-084, January 1998.
6. ASTM D6355-98 Standard Test Method for Human Repeat INSULT Patch Testing of Medical Gloves.

Although the present invention has been described hereinabove by way of preferred embodiments thereof, it can be modified without departing from the spirit and nature of the subject invention as defined in the appended claims.

Having thus described the invention, what is claimed is:

1. A biodegradable multi-component synergistic particulate absorbent composition comprising:
    at least one particle consisting of modified starch selected from the group consisting of cross-linked carboxyalkylated starches, starch maleates and mixture thereof, wherein said modified starch particle has a mean particle size ranging from about 80 microns to about 800 microns; and
    a first component class particle consisting of guar gum having a mean particle size ranging from about 80 microns to about 800 microns,
    a second component class particle consisting of carboxymethyl cellulose having a mean particle size ranging from about 80 microns to about 800 microns,
    wherein said composition is biodegradable and is hypoallergenic according to ASTM method D6355-8.

2. A biodegradable multi-component synergistic particulate absorbent composition as defined in claim 1, exhibiting synergistic effects on absorption under load, centrifuge retention or free swell capacity.

3. A biodegradable multi-component synergistic particulate absorbent composition as defined in claim 1, wherein said modified starches are obtained from the group consisting of corn, waxy corn, wheat, waxy wheat, rice, waxy rice, potato, tapioca, waxy maize, high amylose content corn starch, sorghum, waxy sorghum, sago, barley, amaranth, and mixture thereof.

4. A biodegradable multi-component synergistic particulate absorbent composition as defined in claim 1, wherein said modified starches and said first and second component class particles have a mean particle size ranging from about 150 μm to about 600 μm.

5. A biodegradable multi-component synergistic particulate absorbent composition as defined in claim 4, wherein the mean particle size of said modified starches and of said first and second and component class particles differs by no more than 200 μm.

6. The biodegradable multi-component synergistic particulate absorbent composition of claim 1, wherein the modified starch is a cross-linked carboxyalkylated starch.

7. The biodegradable multi-component synergistic particulate absorbent composition of claim 1, wherein the one or more modified starches are starch maleates.

\* \* \* \* \*